(12) United States Patent
Adams et al.

(10) Patent No.: US 10,973,521 B2
(45) Date of Patent: *Apr. 13, 2021

(54) SURGICAL STAPLER WITH VARIABLE HEIGHT DRIVERS FOR UNIFORM STAPLE FORMATION

(71) Applicant: Ethicon LLC, Guaynabo, PR (US)

(72) Inventors: Thomas E. Adams, Loveland, OH (US); Anil K. Nalagatla, Mason, OH (US); Disha V. Labhasetwar, Cincinnati, OH (US); Barry T. Jamison, Fairfield, OH (US); Mary R. Towers, West Chester, OH (US)

(73) Assignee: Ethicon LLC, Guaynabo, PR (US)

( * ) Notice: Subject to any disclaimer, the term of this patent is extended or adjusted under 35 U.S.C. 154(b) by 125 days.

This patent is subject to a terminal disclaimer.

(21) Appl. No.: 16/292,712

(22) Filed: Mar. 5, 2019

(65) Prior Publication Data
US 2019/0261985 A1 Aug. 29, 2019

Related U.S. Application Data

(63) Continuation of application No. 14/985,549, filed on Dec. 31, 2015, now Pat. No. 10,258,334.

(51) Int. Cl.
*A61B 17/072* (2006.01)
*A61B 17/068* (2006.01)
*A61B 17/00* (2006.01)

(52) U.S. Cl.
CPC ...... *A61B 17/07207* (2013.01); *A61B 17/068* (2013.01); *A61B 17/072* (2013.01);
(Continued)

(58) Field of Classification Search
CPC ... A61B 17/068; A61B 17/072; A61B 17/115; A61B 17/07207; A61B 2017/00818;
(Continued)

(56) References Cited

U.S. PATENT DOCUMENTS 3,494,533 A 2/1970 Green et al.
3,589,589 A 6/1971 Akopov
(Continued)

FOREIGN PATENT DOCUMENTS

CN 101031246 A 9/2007
CN 201 139 594 Y 10/2008
(Continued)

OTHER PUBLICATIONS

European Search Report and Written Opinion dated Feb. 22, 2017 for Application No. EP 16207604.6, 11 pgs.
(Continued)

*Primary Examiner* — Scott A Smith
(74) *Attorney, Agent, or Firm* — Frost Brown Todd LLC

(57) ABSTRACT

A surgical instrument and method for forming a plurality of staples in tissue of a patient includes a body having a firing mechanism, a shaft assembly, an end effector with an anvil, and a cartridge received within the end effector that is operatively connected to the firing mechanism. The cartridge includes a cartridge housing having a plurality of staple slots, a plurality of staples respectively positioned within the plurality of staple slots, and a driver assembly. The driver assembly has a plurality of drivers respectively supporting the plurality of staples within the plurality of staple slots. The firing mechanism is configured to selectively move the plurality of drivers distally toward the anvil for forming the plurality of staples therebetween. At least one driver of the plurality of drivers has a variable distal height relative to at least another driver of the plurality of drivers in a predetermined variable height pattern.

20 Claims, 27 Drawing Sheets

(52) U.S. Cl.
CPC .............. *A61B 2017/00526* (2013.01); *A61B 2017/00818* (2013.01); *A61B 2017/07214* (2013.01); *A61B 2017/07221* (2013.01); *A61B 2017/07242* (2013.01); *A61B 2017/07257* (2013.01); *A61B 2017/07271* (2013.01); *A61B 2017/07278* (2013.01)

(58) Field of Classification Search
CPC ........... A61B 2017/00831; A61B 2017/07221; A61B 2017/07242; A61B 2017/07214; A61B 2017/07271
USPC .............. 227/19, 175.1, 176.1, 178.1, 180.1; 606/139, 153, 219
See application file for complete search history.

(56) References Cited

U.S. PATENT DOCUMENTS

| | | |
|---|---|---|
| 3,795,034 A | 3/1974 | Stekopytov et al. |
| 4,047,654 A | 9/1977 | Alvarado |
| 4,216,891 A | 8/1980 | Behlke |
| 4,354,628 A | 10/1982 | Green |
| 4,527,724 A | 7/1985 | Chow et al. |
| 4,568,009 A | 2/1986 | Green |
| 4,580,712 A | 4/1986 | Green |
| 4,606,345 A | 8/1986 | Dorband et al. |
| 4,607,636 A | 8/1986 | Kula et al. |
| 4,665,916 A | 5/1987 | Green |
| 4,767,044 A | 8/1988 | Green et al. |
| 4,802,614 A | 2/1989 | Green et al. |
| 4,930,503 A | 6/1990 | Pruitt |
| 5,071,052 A | 12/1991 | Rodak et al. |
| 5,403,312 A | 4/1995 | Yates et al. |
| 5,470,009 A | 11/1995 | Rodak |
| 5,673,842 A | 10/1997 | Bittner et al. |
| 6,805,273 B2 | 10/2004 | Bilotti |
| 6,817,508 B1 | 11/2004 | Racenet et al. |
| 6,988,650 B2 | 1/2006 | Schwemberger et al. |
| 7,000,818 B2 | 2/2006 | Shelton et al. |
| 7,134,587 B2 | 11/2006 | Schwemberger et al. |
| 7,147,140 B2 | 12/2006 | Wukusick et al. |
| 7,147,339 B2 | 12/2006 | Schwemberger et al. |
| 7,204,404 B2 | 4/2007 | Nguyen et al. |
| 7,207,472 B2 | 4/2007 | Wukusick et al. |
| 7,407,076 B2 | 8/2008 | Racenet et al. |
| 7,422,139 B2 | 9/2008 | Shelton et al. |
| 7,464,849 B2 | 12/2008 | Shelton et al. |
| 7,669,746 B2 | 3/2010 | Shelton, IV et al. |
| 7,670,334 B2 | 3/2010 | Hueil et al. |
| 7,753,245 B2 | 7/2010 | Boudreaux et al. |
| 7,819,886 B2 | 10/2010 | Whitfield et al. |
| 7,845,537 B2 | 12/2010 | Shelton et al. |
| 7,913,891 B2 | 3/2011 | Doll et al. |
| 7,980,443 B2 | 7/2011 | Scheib et al. |
| 8,210,411 B2 | 7/2012 | Yates et al. |
| 8,308,040 B2 | 11/2012 | Huang et al. |
| 8,317,070 B2 | 11/2012 | Hueil et al. |
| 8,220,688 B2 | 12/2012 | Laurent et al. |
| 8,353,436 B2 | 1/2013 | Kasvikis |
| 8,371,494 B2 | 2/2013 | Racenet et al. |
| 8,393,514 B2 | 3/2013 | Shelton et al. |
| 8,561,870 B2 | 10/2013 | Baxter et al. |
| 8,579,178 B2 | 11/2013 | Holsten et al. |
| 8,608,045 B2 | 12/2013 | Smith et al. |
| 8,714,430 B2 | 5/2014 | Natarajan et al. |
| 8,733,613 B2 | 5/2014 | Huitema et al. |
| 8,827,137 B2 | 9/2014 | Rao |
| 9,072,535 B2 | 7/2015 | Shelton et al. |
| 9,101,358 B2 | 8/2015 | Kerr et al. |
| 9,125,651 B2 | 9/2015 | Mandakolathur Vasudevan et al. |
| 9,198,658 B2 | 12/2015 | Kasvikis |
| 9,566,066 B2 | 2/2017 | Kasvikis |
| 9,700,316 B2 | 7/2017 | Mohan et al. |
| 9,814,460 B2 | 11/2017 | Kimsey et al. |
| 10,045,780 B2 | 8/2018 | Adams et al. |
| 10,194,913 B2 | 2/2019 | Nalagatla et al. |
| 10,258,334 B2 | 4/2019 | Adams et al. |
| 2004/0222268 A1 | 11/2004 | Bilotti et al. |
| 2005/0139636 A1 | 6/2005 | Schwemberger et al. |
| 2005/0143759 A1 | 6/2005 | Kelly |
| 2005/0145672 A1 | 7/2005 | Schwemberger et al. |
| 2005/0247753 A1 | 11/2005 | Kelly et al. |
| 2007/0175955 A1 | 8/2007 | Shelton et al. |
| 2007/0194081 A1 | 8/2007 | Hueil et al. |
| 2013/0334284 A1 | 12/2013 | Swayze et al. |
| 2014/0263551 A1 | 9/2014 | Hall et al. |
| 2014/0263552 A1 | 9/2014 | Hall et al. |
| 2015/0053748 A1 | 2/2015 | Yates et al. |
| 2015/0196347 A1 | 7/2015 | Yates et al. |
| 2017/0189012 A1 | 7/2017 | Adams et al. |
| 2017/0189015 A1 | 7/2017 | Adams et al. |
| 2017/0189021 A1 | 7/2017 | Kimsey et al. |
| 2017/0189132 A1 | 7/2017 | Adams et al. |
| 2019/0000455 A1 | 1/2019 | Adams et al. |
| 2020/0100786 A1 | 4/2020 | Wixey et al. |
| 2020/0205808 A1 | 7/2020 | Adams et al. |

FOREIGN PATENT DOCUMENTS

| | | |
|---|---|---|
| CN | 201445537 U | 5/2010 |
| CN | 202 355 441 U | 8/2012 |
| CN | 103 096 817 A | 5/2013 |
| CN | 103083053 A | 5/2013 |
| CN | 103 906 476 A | 7/2014 |
| CN | 104 169 593 A | 11/2014 |
| CN | 102895010 B | 12/2014 |
| EP | 0246870 A2 | 11/1987 |
| EP | 1550407 A2 | 7/2005 |
| EP | 1550410 A2 | 7/2005 |
| EP | 1550414 A2 | 7/2005 |
| EP | 1723914 A1 | 11/2006 |
| EP | 1997439 A2 | 12/2008 |
| EP | 2090255 A1 | 8/2009 |
| EP | 2165653 A2 | 3/2010 |
| EP | 2248474 A2 | 11/2010 |
| EP | 2839790 A1 | 2/2015 |
| WO | WO 1986/002254 A1 | 4/1986 |
| WO | WO 2015/153340 A2 | 10/2015 |

OTHER PUBLICATIONS

European Search Report and Written Opinion dated Mar. 23, 2017 for Application No. EP 16207608.7, 10 pgs.
European Search Report, Partial, and Written Opinion dated Sep. 14, 2017 for Application No. EP 16207536.0, 11 pgs.
European Search Report and Written Opinion dated Mar. 16, 2017 for Application No. EP 16207619.4, 9 pgs.
European Examination Report dated Jun. 15, 2018 for Application No. EP 16207619.4, 3 pgs.
European Search Report and Written Opinion dated Mar. 13, 2017 for Application No. EP 16207527.9, 7 pgs.
International Search Report and Written Opinion dated Mar. 7, 2017 for Application No. PCT/US2016/066293, 15 pgs.
International Search Report and Written Opinion dated Mar. 23, 2017 for Application No. PCT/US2016/066802, 16 pgs.
International Search Report and Written Opinion dated Jun. 16, 2017 for Application No. PCT/US2016/067429, 13 pgs.
International Search Report and Written Opinion dated Mar. 17, 2017 for Application No. PCT/US2016/067433, 15 pgs.
International Search Report and Written Opinion dated Mar. 13, 2017 for Application No. PCT/US2016/067436, 12 pgs.
U.S. Appl. No. 12/031,573, filed Feb. 14, 2008.
Dictonary.com definition for "head" as accessed Aug. 1, 2019; at https://www.dictionary.com/browse/heads.
European Examination Report dated May 9, 2019 for Application No. EP 16207604.6, 5 pgs.
European Examination Report dated Jun. 13, 2019 for Application No. EP 16207527.9, 5 pgs.
Chinese Office Action, The First Office Action, and Search Report dated Jul. 23, 2020 for Application No. CN 201680077177.9, 10 pgs.

(56) References Cited

OTHER PUBLICATIONS

Chinese Office Action, The First Office Action, and Search Report dated Jul. 20, 2020 for Application No. CN 201680077360.9, 14 pgs.
Chinese Office Action, The First Office Action, and Search Report dated Apr. 22, 2020 for Application No. CN 201680076834.8, 9 pgs.
Chinese Office Action, The First Office Action, and Search Report dated Jul. 16, 2020 for Application No. CN 201680077140.6, 10 pgs.
Chinese Office Action, The First Office Action, and Search Report dated Jun. 30, 2020 for Application No. CN 201680076863.4, 12 pgs.
European Search Report and Written Opinion dated Nov. 29, 2019 for Application No. EP 19203854.5, 10 pgs.
Japanese Notification of Reasons for Refusal dated Dec. 1, 2020 for Application No. 2018-534671, 5 pages.
Japanese Office Action, Notification of Reasons for Refusal, dated Jan. 5, 2021 for Application No. JP 2018-534679, 5 pgs.

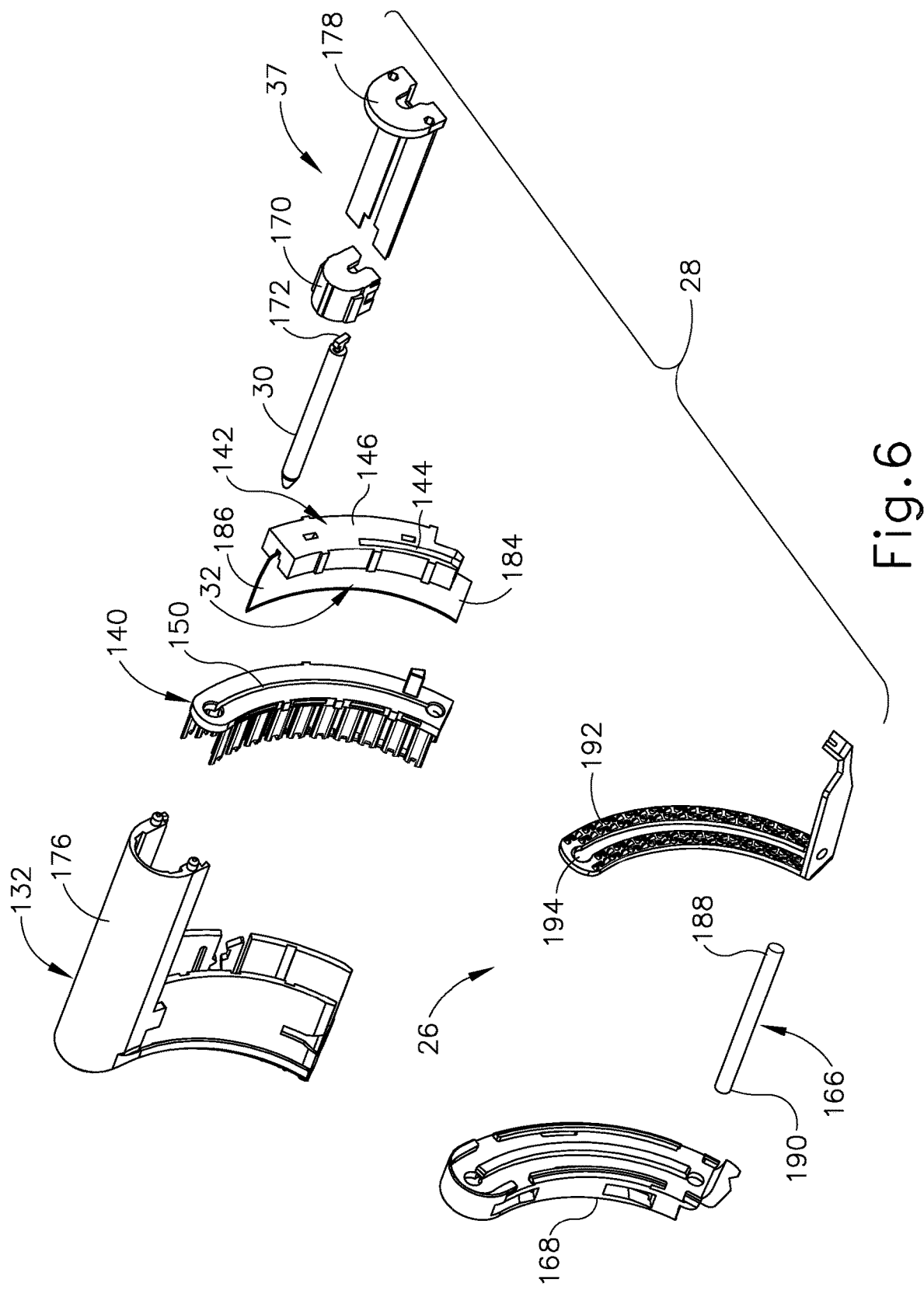

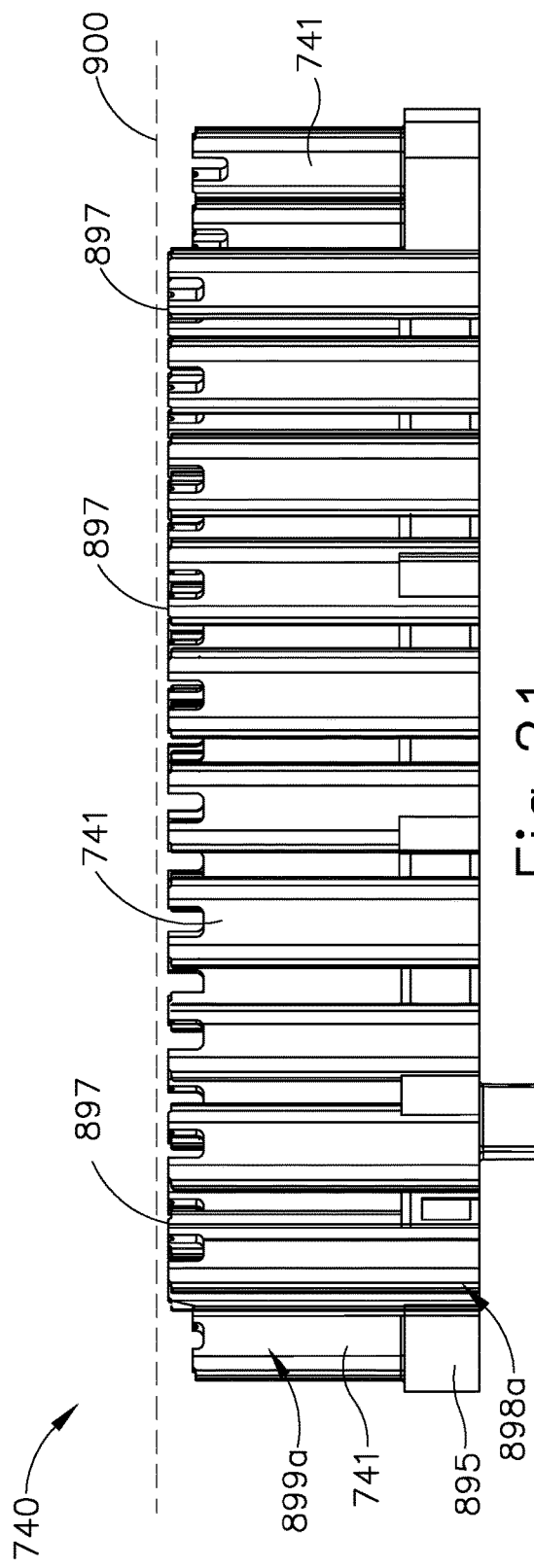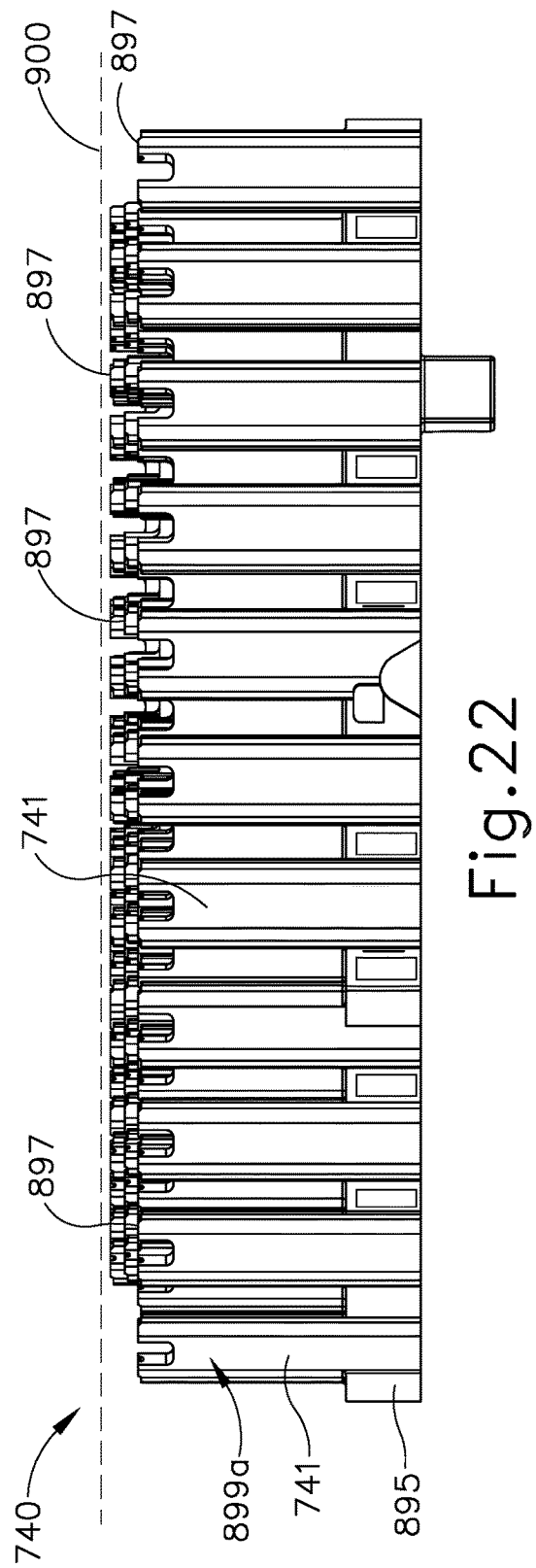

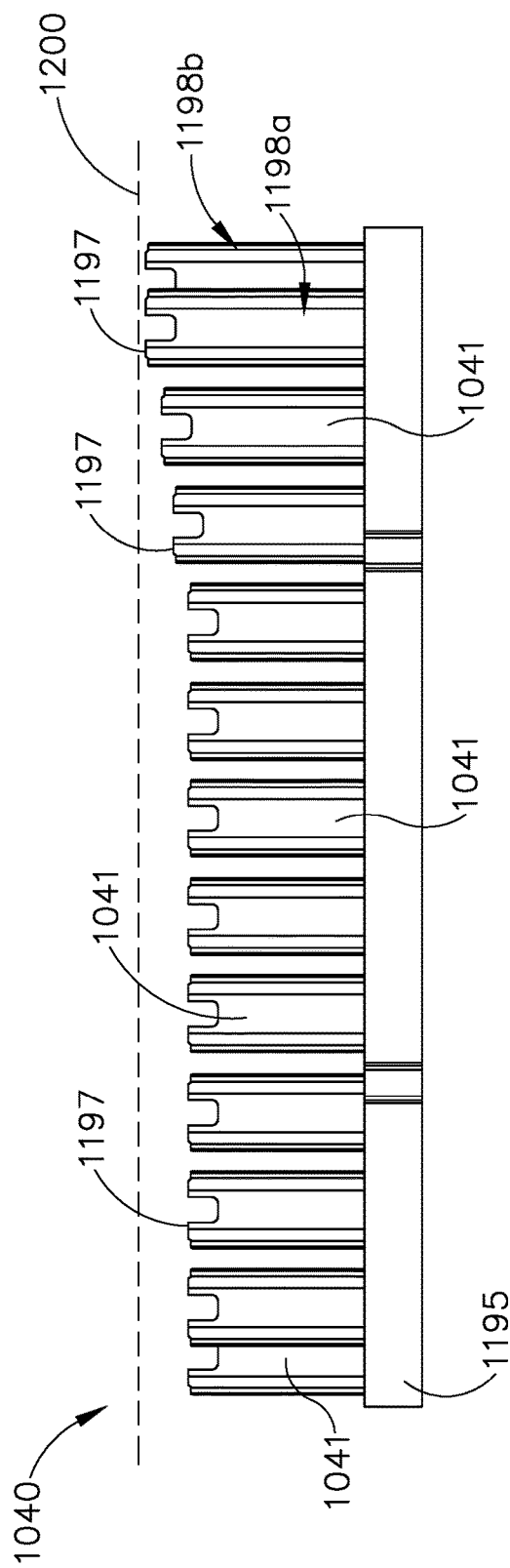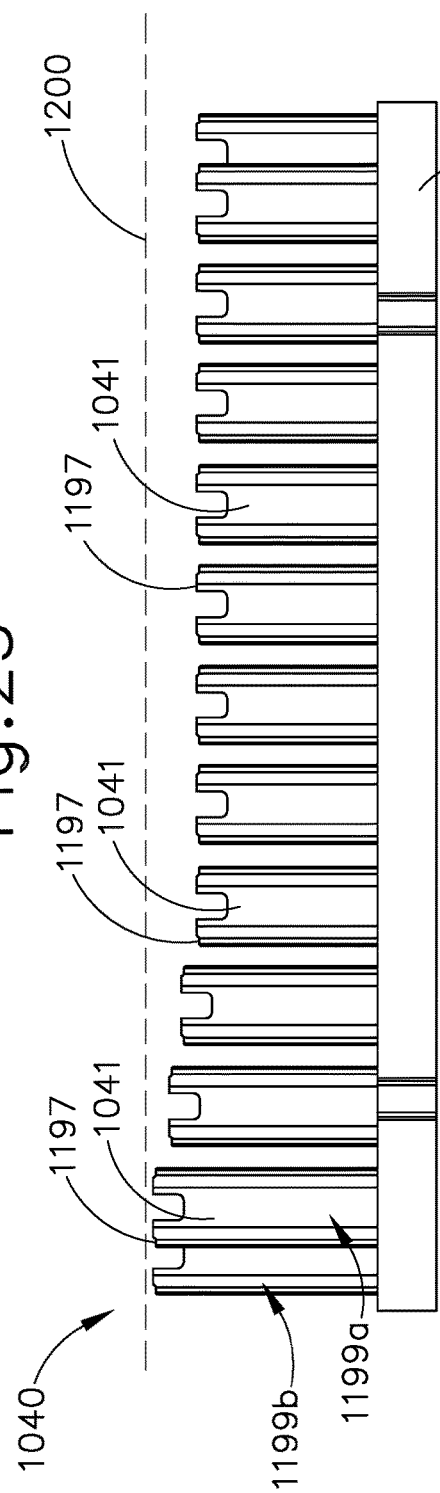

SURGICAL STAPLER WITH VARIABLE HEIGHT DRIVERS FOR UNIFORM STAPLE FORMATION

This patent application is a continuation of U.S. patent application Ser. No. 14/985,549, entitled "Surgical Stapler with Variable Height Drivers For Uniform Staple Formation", filed on Dec. 31, 2015, now U.S. Pat. No. 10,258,334, issued Apr. 16, 2019, the entire disclosure of which is expressly incorporated herein by reference.

BACKGROUND

Some surgical staplers are operable to clamp down on one or more layers of patient tissue, form staples through the layers of tissue to substantially seal the layers of tissue together near the formed staples, and cut through the layers of tissue for forming severed ends of operatively sealed tissue. An exemplary stapling instrument may include a pair of cooperating elongate jaw members, where each jaw member may be adapted to be inserted into a patient and positioned relative to tissue that is to be stapled and/or incised. One of the jaw members may support a staple cartridge with at least two laterally spaced rows of staples contained therein, and the other jaw member may support an anvil with staple-forming pockets aligned with the rows of staples in the staple cartridge. Generally, the stapling instrument may further include a pusher bar and a knife blade that are slidable relative to the jaw members to sequentially or simultaneously eject the staples from the staple cartridge via camming surfaces on the pusher bar and/or camming surfaces on a wedge sled that is pushed by the pusher bar. The camming surfaces may be configured to activate one or more staple drivers carried by the cartridge and associated with the staples in order to push the staples against the anvil and form laterally spaced rows of deformed staples in the tissue gripped between the jaw members. Such rows may be arranged as linear rows and/or arcuate rows for sequentially or simultaneously stapling and cutting the tissue of the patient in the form of a predetermined pattern. The knife blade may trail the camming surfaces and cut the tissue along a linear or arcuate line between the rows of staples formed in the tissue.

Merely exemplary surgical staplers are disclosed in U.S. Pat. No. 6,988,650, entitled "Retaining Pin Lever Advancement Mechanism for a Curved Cutter Stapler," issued Jan. 24, 2006; U.S. Pat. No. 7,134,587, entitled "Knife Retraction Arm for a Curved Cutter Stapler," issued Nov. 14, 2006; U.S. Pat. No. 7,147,139, entitled "Closure Plate Lockout for a Curved Cutter Stapler," issued Dec. 12, 2006, U.S. Pat. No. 7,147,140, entitled "Cartridge Retainer for a Curved Cutter Stapler," issued Dec. 12, 2006; U.S. Pat. No. 7,204,404, entitled "Slotted Pins Guiding Knife in a Curved Cutter Stapler," issued Apr. 17, 2007; and U.S. Pat. No. 7,207,472, entitled "Cartridge with Locking Knife for a Curved Cutter Stapler," issued Apr. 24, 2007. The disclosure of each of the above-cited U.S. Patents is incorporated by reference herein. Additional merely exemplary surgical staplers are disclosed in U.S. Pat. Pub. No. 2005/0139636, entitled "Replaceable Cartridge Module for a Surgical Stapling and Cutting Instrument," published on Jun. 30, 2005, now abandoned; U.S. Pat. Pub. No. 2005/0143759, entitled "Curved Cutter Stapler Shaped for Male Pelvis," published on Jun. 30, 2005, now abandoned; and U.S. Pat. Pub. No. 2005/0145672, entitled "Curved Cutter Stapler with Aligned Tissue Retention Feature," published on Jul. 7, 2005, now abandoned. The disclosure of each of the above-cited U.S. Patent Publications is incorporated by reference herein.

A surgical stapler may be inserted into a patient to perform colorectal surgery. Such procedures may include the use of the stapler to operatively seal, sever, and remove the colon of the patient, in whole or in part. For instance, a proctocolectomy may be performed during a lower anterior resection ("LAR") for treating and inhibiting the spread of colorectal cancer cells. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 6 depicts an exploded rear perspective view of the staple cartridge of FIG. 3;

FIG. 21 depicts a right side view of the staple driver assembly of FIG. 19;

FIG. 22 depicts a left side view of the staple driver assembly of FIG. 19;

FIG. 25 depicts a right side view of the staple driver assembly of FIG. 23; and

FIG. 26 depicts a left side view of the staple driver assembly of FIG. 23.

Figure 1A:
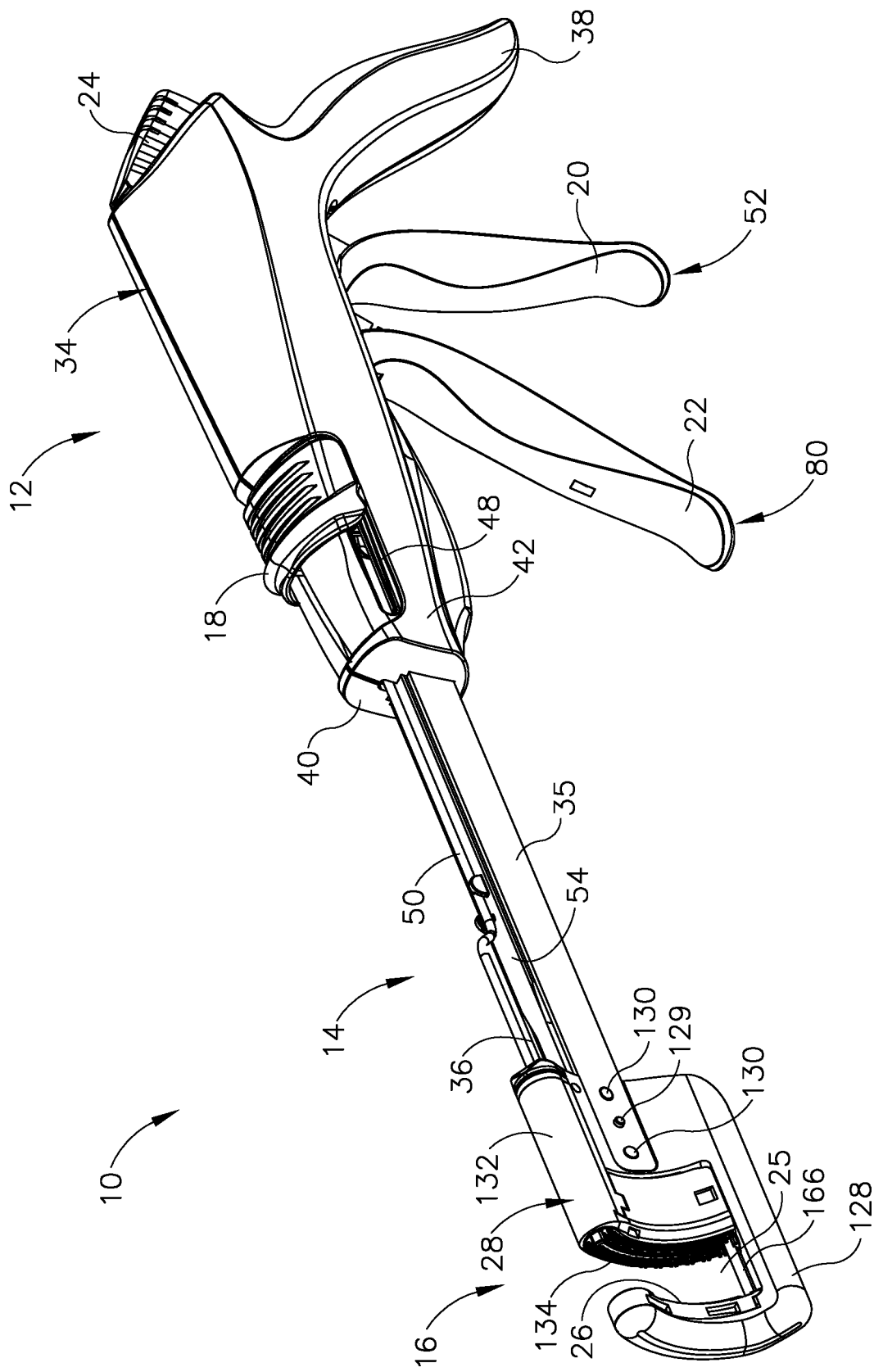
FIG. 1A depicts a right front perspective view of an exemplary surgical stapling instrument with a pin actuation mechanism in an open position and a staple cartridge in open position.

The drawings are not intended to be limiting in any way, and it is contemplated that various embodiments of the invention may be carried out in a variety of other ways, including those not necessarily depicted in the drawings.

The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that for convenience and clarity, spatial terms such as "vertical," "horizontal," "lower," "upper," "front," and "rear" are used herein with respect to the drawings. However, surgical instruments are used in many orientations and positions, and these terms are not intended to be limiting and/or absolute.

I. Exemplary Surgical Stapler

FIG. 1A depicts an exemplary surgical stapling and severing instrument (10) that includes a handle assembly (12), a shaft assembly (14), and an end effector (16) distally projecting from shaft assembly (14). It should be understood that terms such as "proximal," "distal," "right," and "left" are used herein with reference to a clinician gripping handle assembly (12) of surgical stapling instrument (10). Thus, end effector (16) is distal with respect to the relatively proximal handle assembly (14). Except as otherwise described herein, instrument (10) may be configured and operable in accordance with at least some of the teachings of U.S. Pat. Pub. No. 2005/0143759, entitled "Curved Cutter Stapler Shaped for Male Pelvis," published on Jun. 30, 2005, now abandoned, the disclosure of which is incorporated by reference herein; and/or U.S. patent application Ser. No. 14/813,242 entitled "Surgical Instrument Comprising Systems for Assuring the Proper Sequential Operation of the Surgical Instrument," filed on Jul. 30, 2015, issued as U.S. Pat. No.

10,194,913 on Feb. 5, 2019, the disclosure of which is incorporated by reference herein.

Figure 1B:
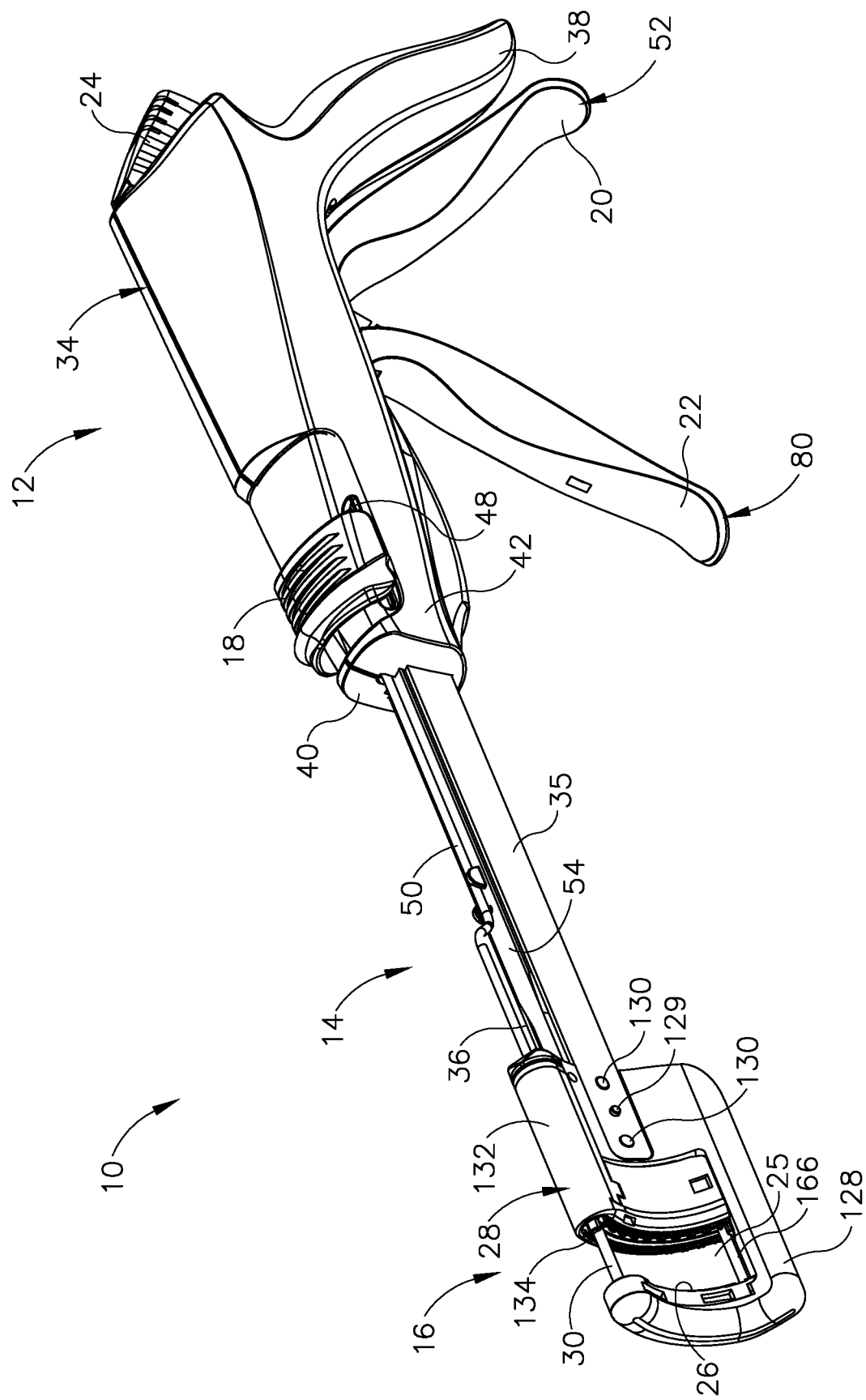
FIG. 1B depicts a right front perspective view of the surgical stapling instrument of FIG. 1A with the pin actuation mechanism in a closed position and the staple cartridge in the open position.

Handle assembly (12) includes several actuation mechanisms for operating end effector (16) during the surgical procedure. To this end, exemplary handle assembly (12) includes a saddle shaped slide (18), a closure trigger (20), and a firing trigger (22) in communication with end effector (16) via shaft assembly (14). As shown in FIG. 1A, slide (18) and closure trigger (20) are in open configurations such that end effector (16) is configured to receive tissue laterally within a gap (25) between an anvil (26) and a cartridge (28) of end effector (16). Translating slide (18) distally toward end effector (16) slides a retaining pin (30) of end effector distally as shown in FIG. 1B for capturing the tissue between anvil (26) and cartridge (28). With respect to FIGS. 1C and 1D, sequentially actuating closure trigger (20) and firing trigger (22) respectively compresses the tissue between anvil (26) and cartridge (28) in a closed configuration and then forms a plurality of staples (not shown) within the tissue and severs the tissue with a knife (32) (see FIG. 6) for treatment. Additional details regarding these exemplary actuation mechanisms will be provided below in greater detail.

A. Exemplary Handle Assembly and Shaft Assembly

Figure 2A:
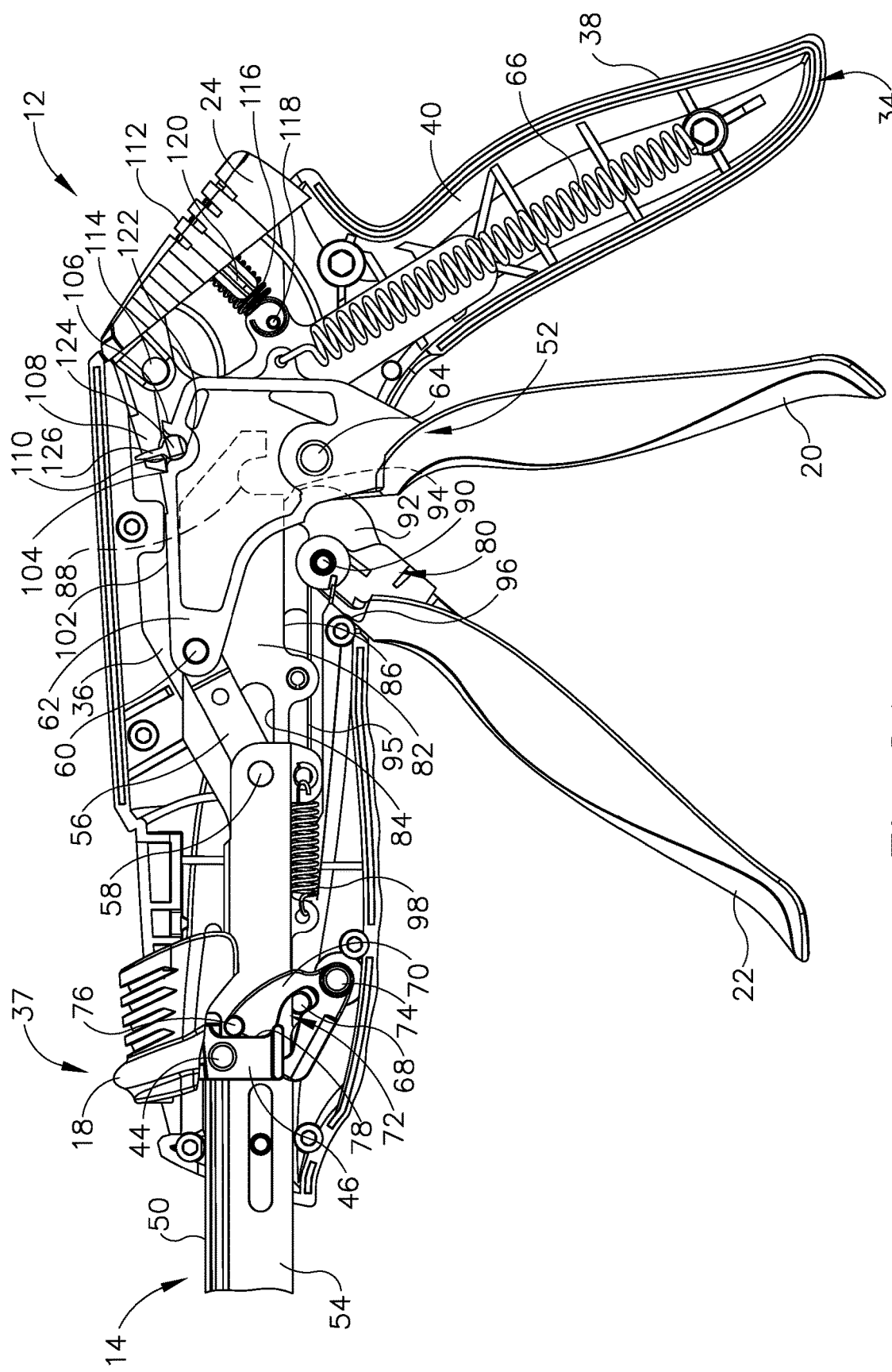
FIG. 2A depicts a right side view of a handle assembly of the surgical stapling instrument of FIG. 1A, with various components removed for clarity, and with the pin actuation mechanism in a closed position and the staple cartridge in the open position.

As shown in FIGS. 1A and 2A, handle assembly (12) has a handle housing (34), a pair of handle frame plates (35, 36) within handle housing (34) extending along shaft assembly (14), saddle shaped slide (18), closure trigger (20), and firing trigger (22) as briefly discussed above. Handle housing (34) defines a hand grip (38), which the operator, such as a surgeon, grasps with the palm of at least one hand. Handle housing (34) is formed by a right shroud handle portion (40) and a left shroud handle portion (42). Closure trigger (20) is proximally positioned relative to firing trigger (22) and each are pivotally mounted to frame plates (35, 36) to extend underneath a remainder of handle assembly (12) for manipulation by the fingers of the operator. Closure and firing triggers (20, 22) are shown in unactuated positions prior to closing end effector (16) and firing staples (not shown) and/or knife (32) (see FIG. 6). Consequently, cartridge (28) is spaced from anvil (26) for receiving tissue within gap (25) therebetween.

Surgical stapling instrument (10) captures tissue via a tissue retaining pin actuation mechanism (37) prior to actuation of the closure and firing triggers (20, 22). FIG. 1A shows retaining pin actuation mechanism (37), which includes slide (18), in the open configuration, whereas FIG. 2A shows retaining pin actuation mechanism (37) in the closed configuration in greater detail. With respect to FIG. 2A, slide (18) is mounted on an upper surface of handle housing (34) and is configured to linearly translate between proximal and distal positions. Slide (18) connects to posts (44), which extend laterally outwardly from a push rod driver (46), through slots (48) (see FIG. 1A). Push rod driver (46) is restrained within handle housing (34) along longitudinal movement by slots (48). Push rod driver (46) is connected to a proximal end of a push rod (50). A distal end of push rod (50) connects to retaining pin (30) (see FIG. 6) such that distal movement of slide (18) causes push rod (50) to similarly slide proximally along shaft assembly (14) for moving retaining pin (30) (see FIG. 6) to the closed configuration, which will be discussed below in greater detail.

A closure mechanism (52), which includes closure trigger (20), is configured to selectively move cartridge (28) toward the tissue positioned between anvil (26) and cartridge (28) in the closed configuration in anticipation of stapling and/or cutting the tissue. Closure mechanism (52) further includes an elongated closure member (54), with a generally U-shaped cross-section, extending distally from handle assembly (12), through shaft assembly (14), and into end effector (16) for receiving a cartridge (28) (see FIG. 3) at a distal end portion thereof as discussed below. A proximal end portion of closure member (54) is operatively connected to closure trigger (20) by a plurality of linkages configured to convert pivoting motion of closure trigger (20) into translation of closure member (54). More particularly, the intermediate and proximal end portions of closure member (54) extend through handle assembly (12) between left and right handle frame plates (35, 36). Right and left closure links (56) are respectively pivotally attached at the right and left proximal ends of closure member (54) by an integral closure link pin (58). At an opposite end of the closure links (56), closure links (56) are pivotally attached to another integral closure link pin (60). Closure link pin (60) connects closure links (56) to a slotted closure arm link (62), which is pivotally mounted to handle frame plates (35, 36) at a closure trigger pin (64). Closure trigger (20) descends from the slotted closure arm link (62) for pivotal rotation about closure trigger pivot pin (64) both toward and away from hand grip (38). A closure spring (66) housed within hand grip (38) is secured to the slotted closure arm link (62) to provide a desired resistance when the operator squeezes closure trigger (20) toward hand grip (38), and to bias closure trigger (20) toward the open position.

Closure member (54) is further configured for directing movement of tissue retaining pin actuation mechanism (37) to automatically direct movement of the retaining pin (30) to the closed configuration while the operator squeezes closure trigger (20). Such automation may be useful in the event that the operator did not manually move the slide (18) to the distal position before actuating trigger (20). Closure member (54) includes posts (68), which extend laterally on each opposing side of closure member (54) within handle housing (34). Posts (68) slidably connect to a yoke (70) via L-shaped slots (72). Yoke (70) is pivotally mounted within handle housing (34) by a pivot pin (74). Yoke (70) further includes cam pins (76) that are configured to push camming surfaces (78) on push rod driver (46). Thus, actuating closure trigger (20) to an intermediate position shown in FIG. 2A directs the closure member (52) distally and, in turn, causes yoke (70) to engage push rod driver (46) and force retaining pin (30) (see FIG. 1B) to the closed position. Slide (18) is thereby dragged along handle housing (34) from the proximal position to the distal position in the event that the operator did not manually manipulate slide (18) to the distal position before actuating trigger (20).

Figure 1C:
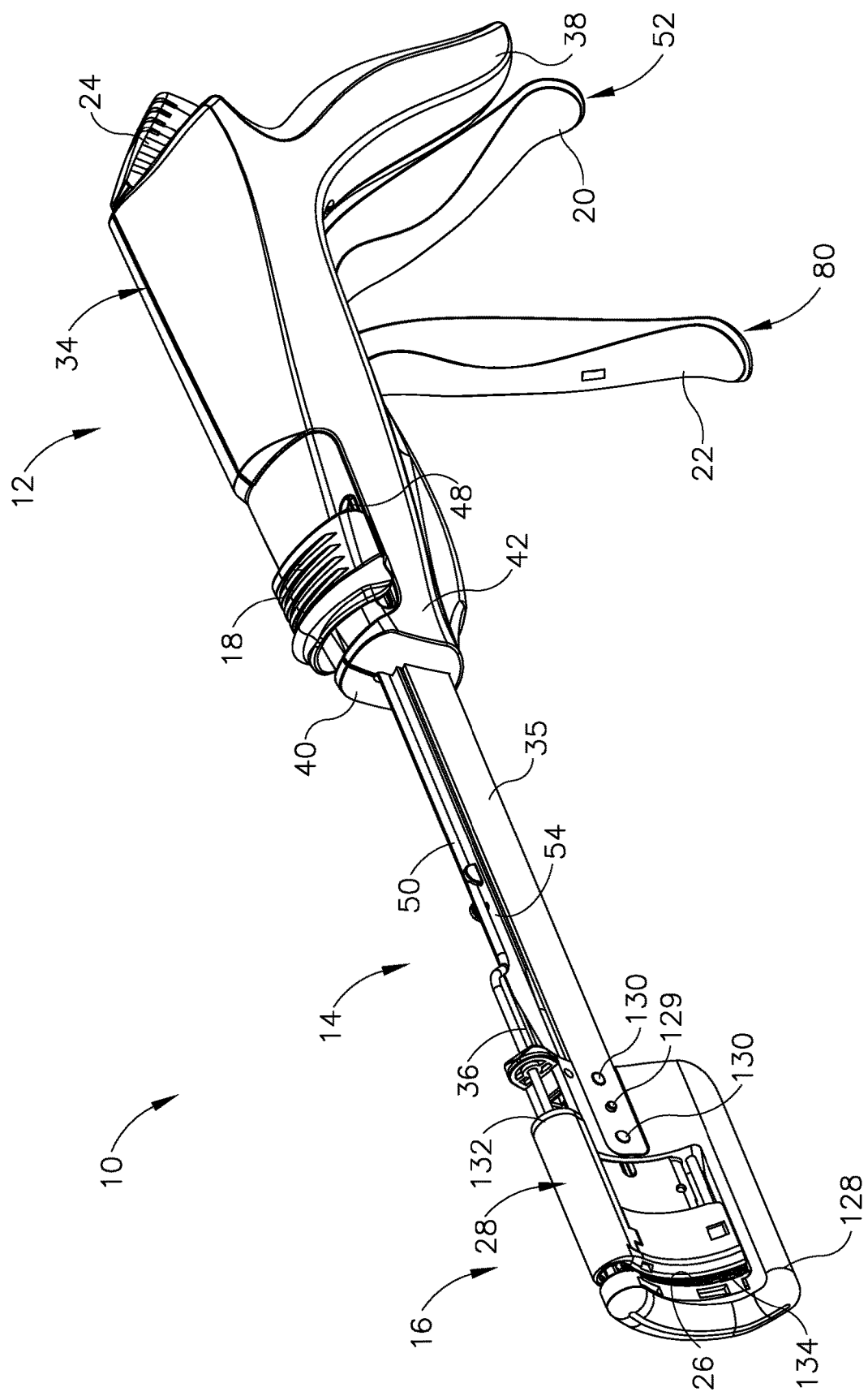
FIG. 1C depicts a right front perspective view of the surgical stapling instrument of FIG. 1A with the pin actuation mechanism in the closed position and the staple cartridge in a closed position via actuation of a closure mechanism.
Figure 1D:
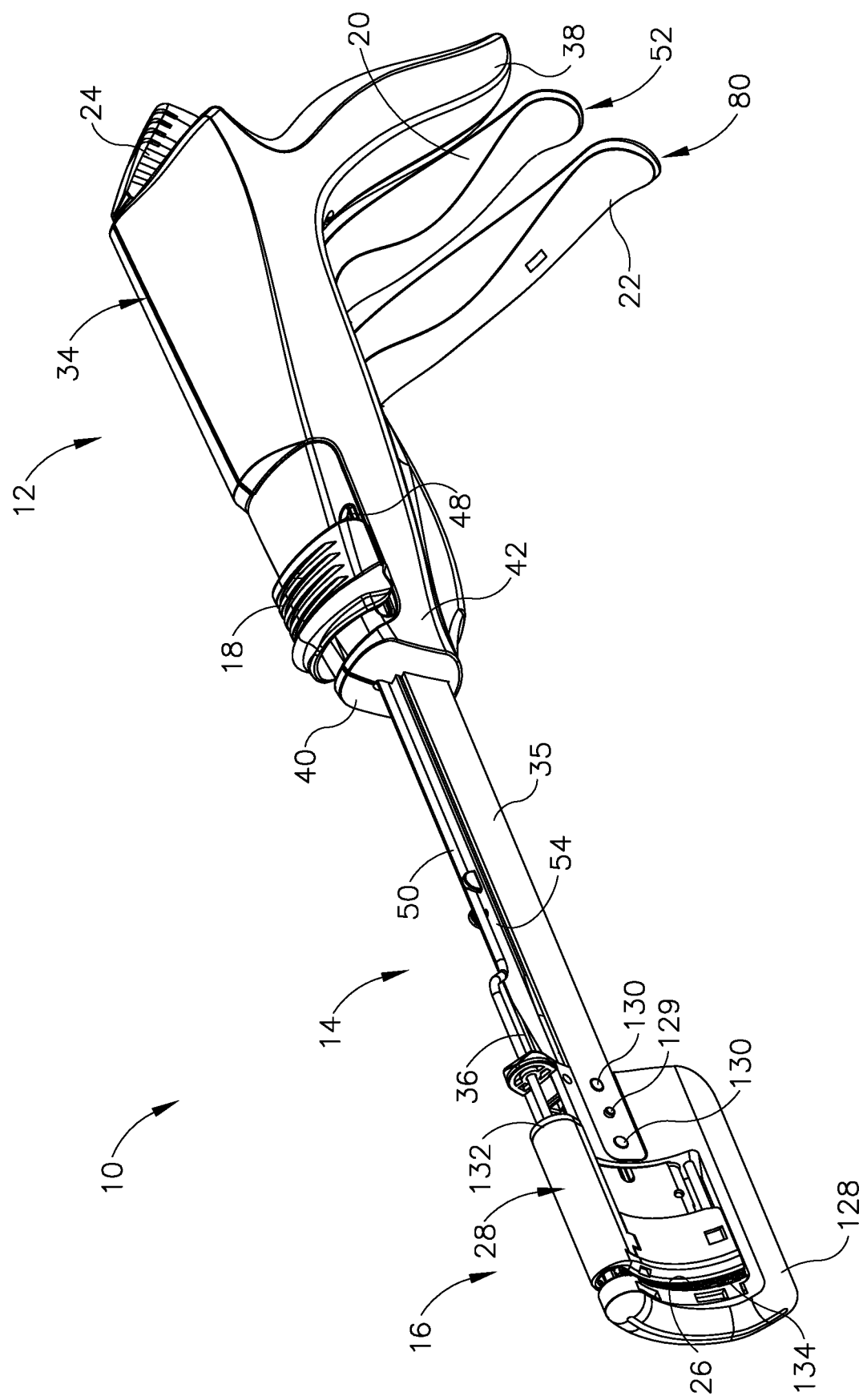
FIG. 1D depicts a right front perspective view of the surgical stapling instrument of FIG. 1A with the pin actuation mechanism and the staple cartridge in the closed positions and a firing trigger in a fired position for stapling and cutting tissue of a patient.
Figure 2B:
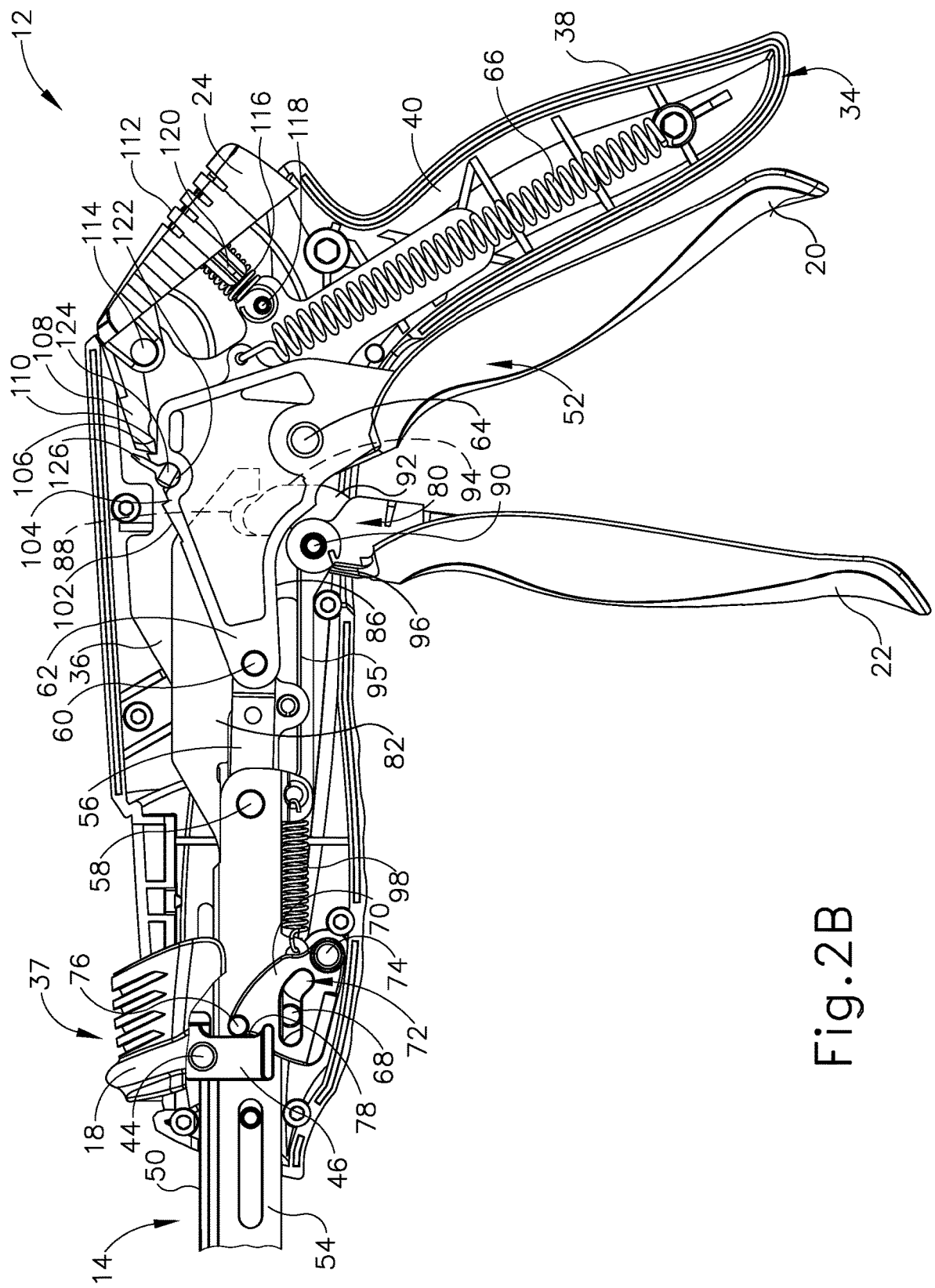
FIG. 2B depicts a right side view of the handle assembly of the surgical stapling instrument of FIG. 1A, with various components removed for clarity, and with the pin actuation mechanism in the closed position and the staple cartridge in the closed position via actuation of the closure mechanism.
Figure 2C:
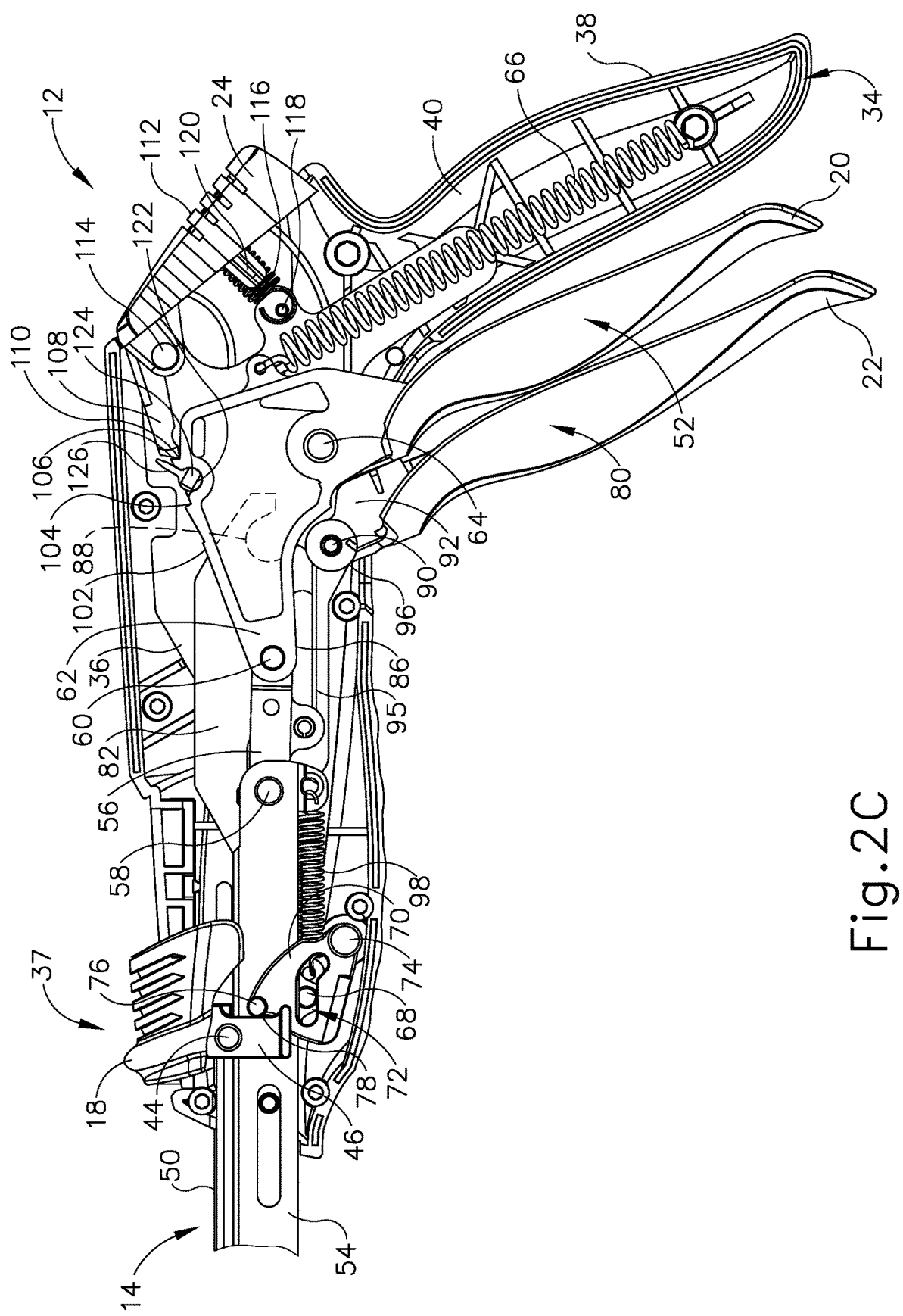
FIG. 2C depicts a right side view of the handle assembly of the surgical stapling instrument of FIG. 1A, with various components removed for clarity, and with the pin actuation mechanism and the staple cartridge in the closed positions and the firing trigger in the fired position for stapling and cutting tissue of a patient.

The operator further squeezes the closure trigger (20) to the hand grip (38) as shown in FIGS. 1C and 2B to effectively set surgical stapling instrument (10) in the closed configuration prior to forming the staples (not shown) and severing the tissue as discussed briefly above. Exemplary handle assembly (12) is configured to form the staples (not shown) and sever the tissue via a firing mechanism (80) upon operator manipulation of firing trigger (22) toward closure trigger (20) as shown in FIGS. 1D and 2C. With respect to FIGS. 1C, 1D, 2B, and 2C, firing mechanism (80), which includes firing trigger (22), has a firing bar (82) extending distally from handle assembly (12) and within end effector (16). A distal end of firing bar (82) cooperates with cartridge (28) as discussed below in greater detail, whereas a proximal end of firing bar (82) is operatively connected to firing trigger (80) for selective firing thereof.

Firing bar (82) has a rectangular receiving slot (84) (see FIG. 2A) in a portion of firing bar (82) positioned within handle housing (34). Integral closure link pin (58) extends through receiving slot (84). The underside of the proximal end portion of firing bar (82) has a sliding surface (86). The proximal end portion of firing bar (82) also has a terminal side engagement surface (82) extending from sliding surface (86). Firing trigger (22) is pivotally mounted to handle frame plates (35, 36) by a firing trigger pin (90) spaced from closure trigger pin (64) such that each of pins (90, 64) pivot about mutually independent axes. Firing trigger (22) includes an arcuate firing trigger link (92) extending from firing trigger (22) at firing trigger pin (90) to an apex (94), which rests on sliding surface (86) of the proximal end portion of firing bar (82). Within handle assembly (12), firing trigger (22) is attached to firing trigger spring arms (95, 96), respectively. Firing trigger spring arms (95, 96) support a torsion spring (not shown) on the right half of firing trigger (22). Finally, a firing bar return spring (98) is secured to the underside of firing bar (82) at the portion of firing bar (82) within handle assembly (12) to bias firing bar (82) toward its unactuated position.

As the operator squeezes closure trigger (20) toward hand grip (38), slotted closure arm link (62) and closure links (56) move distally within receiving slot (84) of firing bar (82). This distal movement causes closure member (54) to correspondingly move distally. Likewise, firing bar (82) concurrently moves distally with closure member (54), because integral closure link pin (58), to which closure links (56) are attached, extends through receiving slot (84) in firing bar (82) (see FIG. 2A). Thereby, firing bar (82) is forced distally to form the staples (not shown) in the tissue and/or sever the tissue with knife (32) (see FIG. 6). Finally, the operator may fully squeeze firing trigger (22) toward hand grip (38) to "fire" surgical stapling instrument (10) and force firing bar (82) further distally to form the staples (not shown) and sever the tissue. This distal movement of firing bar (82) may also be referred to herein as "firing" the firing bar (82) to the actuated or "fired" position.

Upon operator release of one or both of closure and firing triggers (20, 22) while one or both of triggers (20, 22) is/are in a fired position, or in an intermediate position between the unactuated and fired positions, surgical stapling instrument (10) may be further configured to releasably lock in one of a variety of configurations. The operator may then release the hand grip (38) to free one or more hands for another task during the surgical procedure and, when desired, release surgical stapling instrument (10) from its locked position by release button (24). By way of example, surgical stapling instrument (10) has an intermediate closure detent position and a closure detent position. With respect to FIGS. 2A-2C, the top side of the slotted closure arm link (62) has a clamp sliding surface (102) that displays an intermediate detent (104) and a closure detent (106). A release pawl (108) slides on clamp sliding surface (102) and may engage intermediate and closure detents (104,106). Release pawl (108) has a laterally extending pawl lug (110) at its distal end.

Release pawl (108) is located within handle assembly (12) and is integrally formed with release button (24), which is situated exterior of handle housing (34) for manipulation by the operator. Release button (24) has a thumb rest (112) pivotally attached to handle housing (34) by a release trunnion (114). Release button (24) is biased outwardly from handle housing (34) and, therefore, release pawl (108) is biased downwardly toward clamp sliding surface (102) by a release spring (116). Release spring (116) is mounted to handle housing (34) by a spring retention pin (118) and is mounted to release button (24) by a button spring post (120). Slotted closure arm link (62) has an arcuate recess (122) located between intermediate and closure detents (104, 106).

Resting within arcuate recess (122) for rotational movement are integrally connected left and right hand toggles (124). Each toggle (124) has a toggle arm (126) that is engageable with pawl lug (110).

In order to releasably lock handle assembly (12), toggle arms (126) from pawl lug (110) disengage from pawl lug (110) as closure trigger (20) is squeezed toward hand grip (38). Consequently, as toggle (124) continues to rotate in a clockwise direction, release pawl lug (108) rides up toggle arms (126) and, with continued motion of closure trigger (20), falls into one of intermediate and closure detents (104, 106), depending on the position of closure trigger (20) in use. As release pawl (108) rides up toggle arm (126), release pawl (108) rotates release button (24) clockwise. Release pawl (108) thereby falls into one of intermediate and detents (104, 106) and generates an audible clicking sound alerting the surgeon that one of the intermediate and closure positions have been reached.

In order to release handle assembly (12) from the intermediate or closure positions discussed herein, the surgeon depresses release button (24). In turn, release pawl (108) pivots about release trunnion (114) in a clockwise direction to dislodge pawl lug (110) from one of the intermediate and closure detents (104, 106). As pawl lug (110) is dislodged, pawl lug (110) rides on toggle arms (126) to another position, such as the unactuated position. Therefore, the operator may release closure and firing triggers (20, 22) such that each may return to the unactuated positions FIG. 1A and FIG. 3.

Surgical stapling instrument (10) of the present example includes each of handle frame plates (35, 36), push rod (50), closure member (54), and firing bar (82) extending continuously from handle assembly (12) to end effector (16), thereby defining shaft assembly (14) extending therebetween. Handle frame plates (35, 36), push rod (50), closure member (54), and firing bar (82) of surgical stapling instrument (10) provide merely a subset of elongated components extending distally from handle assembly (12) as shaft assembly (14). Alternatively, shaft assembly (14) may include additional components, such as an articulating joint, or may include a rearrangement of various components such that shaft assembly (14) may be modular relative to handle assembly (12). In any case, it will be appreciated that the invention is not intended to be limited to shaft assembly (14) described herein, and may include various alternative arrangements for operatively connecting end effector (16) to handle assembly (12). Of course, handle assembly (12) and shaft assembly (14) may have a variety of other components, features, and operabilities, in addition to or in lieu of any of those noted above. Other suitable configurations for handle and shaft assemblies (12, 14) will be apparent to those of ordinary skill in the art in view of the teachings herein.

B. Exemplary End Effector

Figure 3:
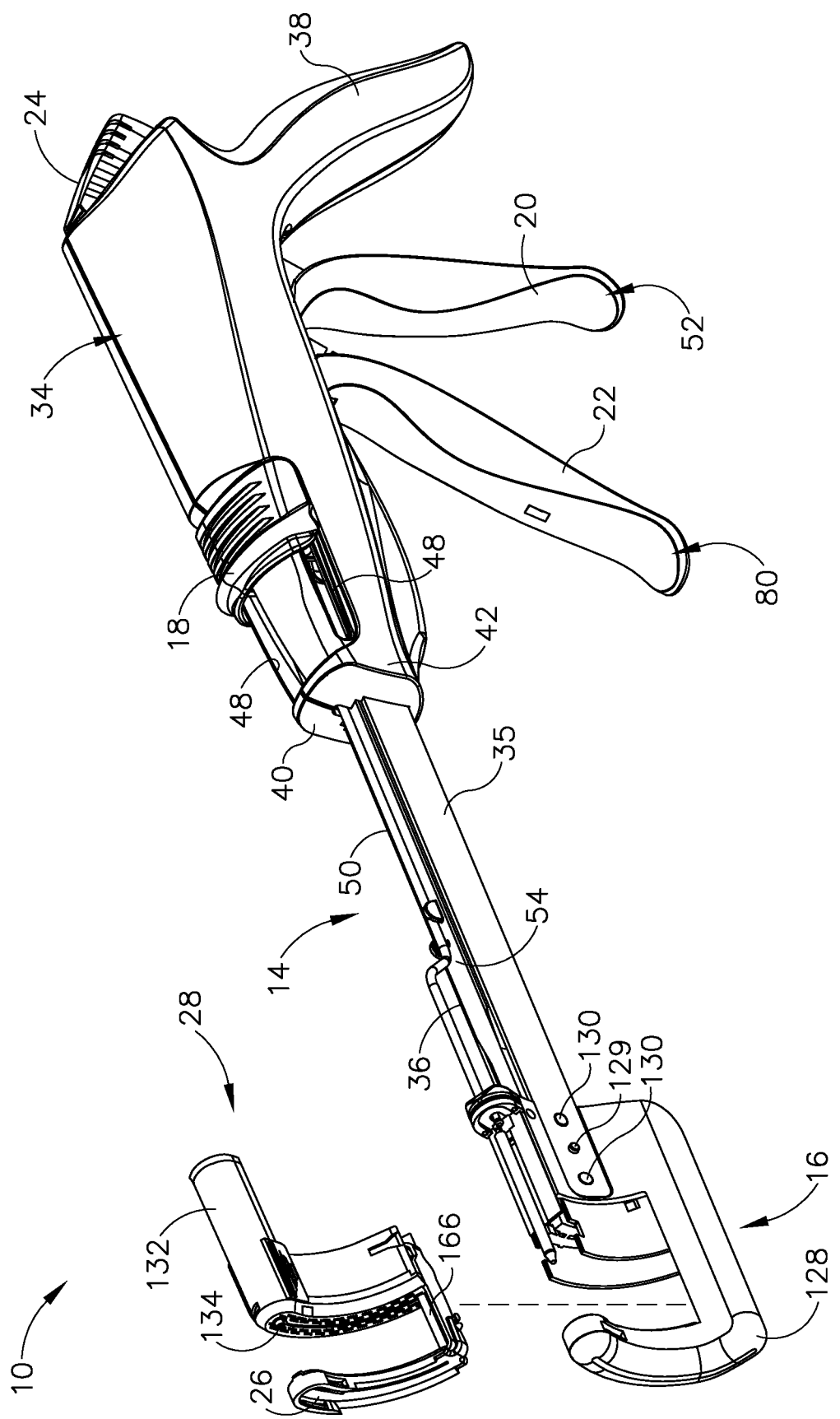
FIG. 3 depicts a partially exploded right front perspective view of the surgical stapling instrument of FIG. 1A showing the staple cartridge removed from a remainder of an end effector.
Figure 4:
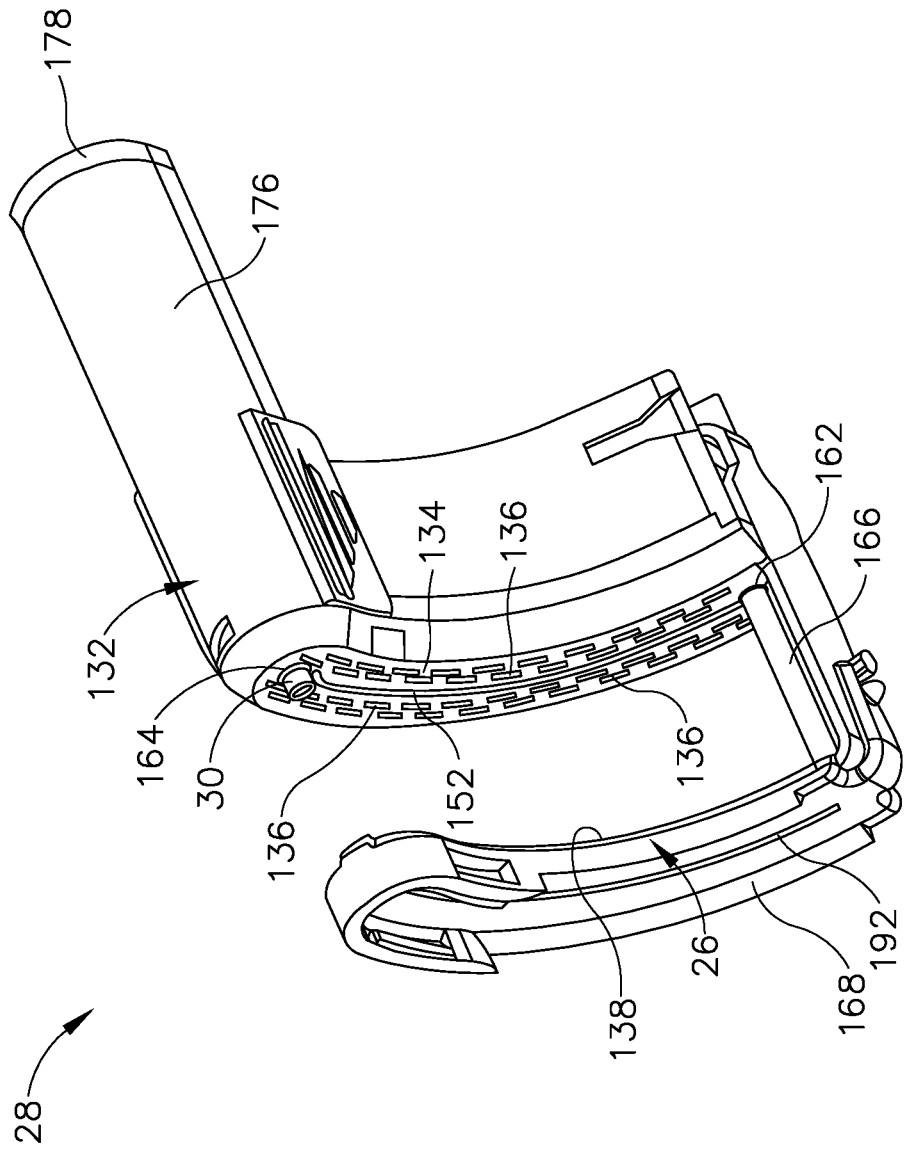
FIG. 4 depicts a right front perspective view of the staple cartridge of FIG. 3.
Figure 5:
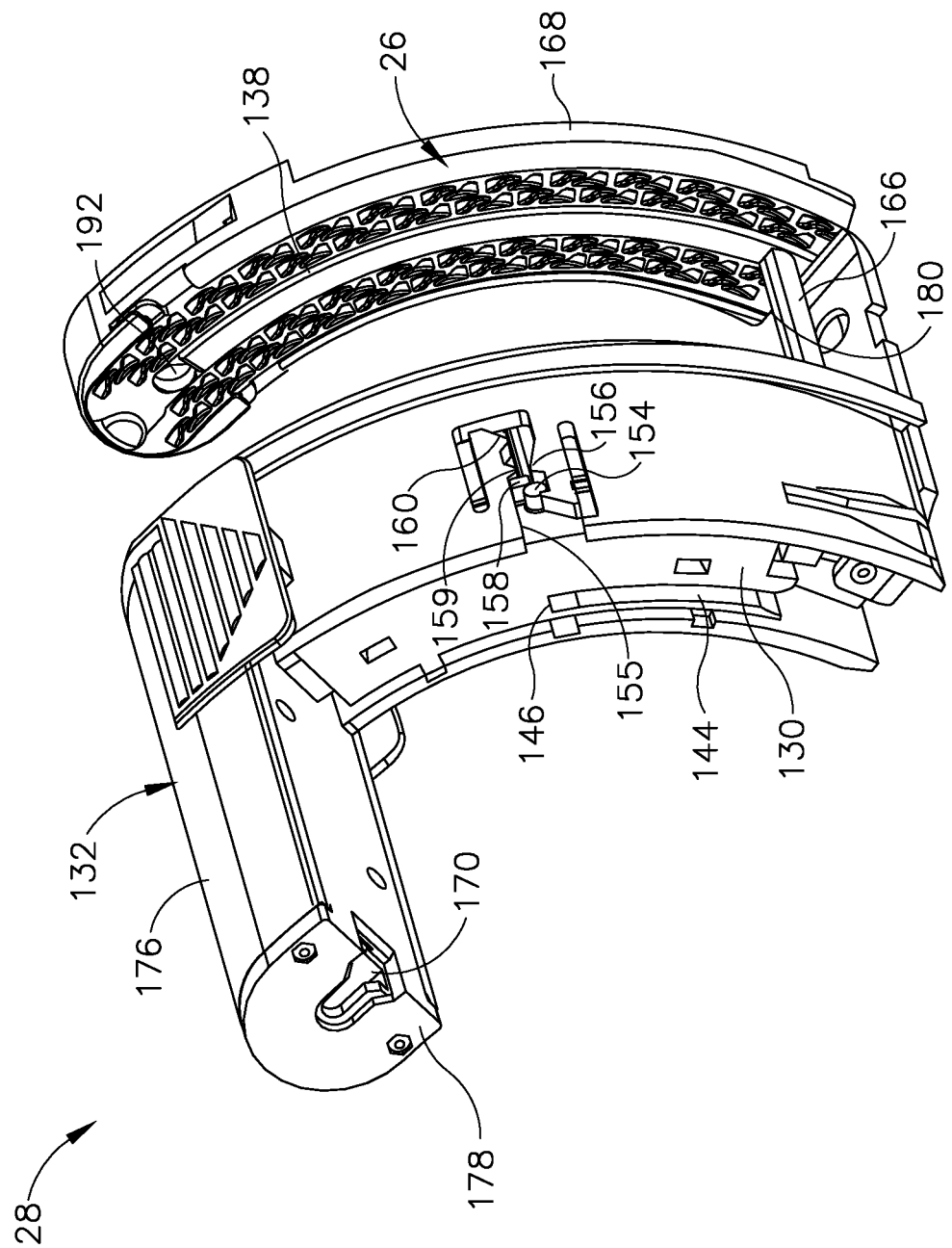
FIG. 5 depicts a rear perspective view of the staple cartridge of FIG. 3.

As also shown in FIGS. 3-5 and discussed briefly above, end effector (16) of the present example includes anvil (26), replaceable cartridge (28) including a plurality of staples (not shown) and knife (32) (see FIG. 6), and retainer pin (30). While end effector (16) of the present example is adapted for use in conjunction with replaceable cartridge (28) having various components, it will be appreciated that the concepts underlying the present invention could be applied to a variety of end effector and cartridge constructions for treating the patient.

End effector (16) provides a surgical fastening assembly that includes cartridge (28) received within a C-shaped supporting structure (128). The term C-shaped is used throughout the specification to describe the concave nature of supporting structure (128) and cartridge (28). The C-shaped construction facilitates enhanced functionality and access to tissue within the patient. The term "C-shaped" as used herein should be construed to include a variety of concave shapes that would similarly enhance the functionality of surgical stapling and cutting instruments. By way of example only, the C-shape of supporting structure (128) may be sized to promote access to the lower colon within the pelvic bowl of a patient, such as to perform a LAR in a proctocolectomy procedure.

Supporting structure (128) of end effector (16) is respectively attached to handle frame plates (35, 36) of shaft assembly (14) by a shoulder rivet (129) and posts (130) which extend from supporting structure (128) into receiving holes in handle frame plates (35, 36). The distal end of closure member (54) is disposed to receive cartridge (28) thereon for directing cartridge (28) to the closed configuration. Upon return of cartridge (28) from the closed configuration to the open configuration, cartridge (28) further includes a safety lockout mechanism (131) (see FIG. 7A) configured to inhibit inadvertently re-firing cartridge (28). Safety lockout mechanism (131) will be discussed below in additional detail.

Cartridge (28) includes anvil (26) coupled to a cartridge housing (132). Cartridge (28) also includes retaining pin (30) and a tissue contacting surface (34), which defines a plurality of staple-containing slots (136) in staggered formation in one or more rows on either side of knife (32) (see FIG. 6). Staples (not shown) are fired from cartridge housing (132) against a staple-forming surface (138) of anvil (26) that faces tissue-contacting surface (134) of cartridge housing (132). Cartridge (28) may also include a removable retainer (not shown) for storage between anvil (26) and tissue contacting surface (34) prior to and/or after use in order to inhibit unintended contact with various portions of cartridge (28).

As shown in FIGS. 4-6, cartridge (28) includes a staple driver assembly (140) within cartridge housing (132) and proximally positioned behind the plurality of staples (not shown) within staple-containing slots (136). Driver assembly (140) of the present example is formed as a unitary structure of a plurality of staple drivers (141). Thus, the term "assembly" is not intended to be limited to an assembly of individual components, but may also include integrally formed components with unitary structures. Driver assembly (140) is configured to push the staples (not shown) respectively out of staple containing slots (136) and toward anvil (26) for formation. A knife holder (142) is disposed immediately proximal of driver assembly (140) in cartridge housing (132) and defines a slot (144) and ledge (146) for interaction with a knife retractor hook (148) (see FIG. 10B), which is discussed below in greater detail. Knife holder (142) is attached to knife (32) such that knife (32) extends distally from knife holder (142) through a slot (150) in driver assembly (140) and through another slot (152) in cartridge housing (132). Although knife (32) is disclosed as being within cartridge housing (132) in the present example, other configurations may also be used. For example, it will be appreciated that cartridge (28) may alternatively not include knife (32) for alternative treatments.

Knife holder (142) has a detent post (154) that extends through a slot (155) in cartridge housing (132). Detent post (154) is positioned in order to contact a detent protrusion (156) of cartridge slot (155) during the longitudinal travel of knife (132) and knife holder (142). Similarly, driver assembly (140) has a detent post (158) positioned in order to contact proximal and distal detent protrusions (159, 160) of cartridge slot (155).

Knife (32) and slots (150, 152) are positioned such that there is at least one row of staples (not shown) on either side of knife (132). In some versions, two rows of staple slots (136) containing respective rows of staples (not shown) are provided on each side of slot (152) of cartridge housing (132).

Cartridge housing (132) defines two longitudinally extending, generally circular holes (162, 164) at respective ends of knife slot (152). More particularly, hole (162) at a lower portion of cartridge housing (132) is shaped and dimensioned to receive a guide pin (166) through cartridge housing (132). Hole (164) at an upper portion of cartridge housing (132) is shaped and dimensioned to slidably receive retaining pin (30) through cartridge housing (132). Staple slots (136) of the present example are arranged such that the staples (not shown) laterally extend past the generally circular holes (162, 164).

Anvil (26) of the present example includes a plastic cutting washer (168) and a metallic staple-forming surface (138). Anvil (26) is disposed to maintain staple-forming surface (138) in alignment with the staples (not shown) to receive and form the staples (not shown) thereon. Retaining pin (30) is connected to a couplet (170) by a circumferential slot (172) in retaining pin (30) and a groove (not shown) in couplet (170). Couplet (170) is disposed within an arm (176) of cartridge housing (132) and is secured to arm (176) by an end cap (178).

Guide pin (166) and retaining pin (30) include respective slots (180, 182) (see also FIGS. 8-9) into which lower and upper ends (184, 186) of knife (32) are slidably disposed. A proximal end (188) of guide pin (166) is connected to anvil (26), whereas a distal end (190) of guide pin (166) extends from cartridge housing (132) and extends through a slot (192) in anvil (26). Cutting washer (168) slips onto anvil (26) via groove (194). Thereby, cutting washer (168) is configured to trap guide pin (166) in the opening formed by slot (192) in anvil (26) and a cutting surface (157) of anvil (26) for connecting anvil (26) to cartridge housing (132).

Figure 7A:
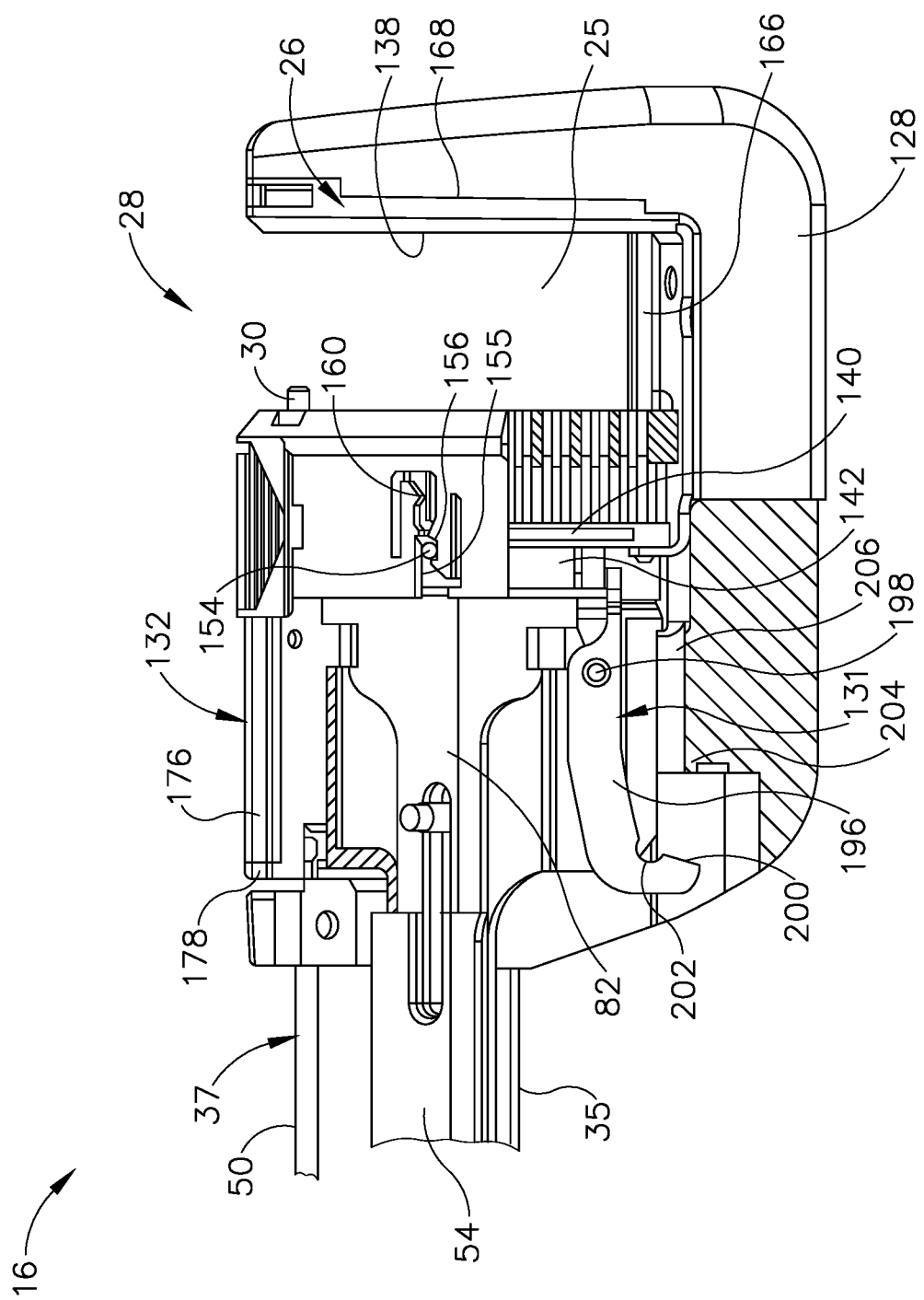
FIG. 7A depicts a left side view of the end effector of FIG. 1A with various components removed for clarity.

Lockout mechanism (131) is shown in FIG. 7A in greater detail. Lockout mechanism (131) is configured to inhibit full proximal movement of cartridge housing (132) to its unactuated position after firing. To this end, lockout mechanism (131) of the present example includes a lockout lever (196) that is pivotally mounted to the distal end of closure member (54) by a pin (198). Lockout lever (196) is spring biased toward the proximal end portion of supporting structure (128) by a spring (not shown). A proximal end portion of lockout lever (196) has a cam surface (200) and a locking groove (202). Supporting structure (128) of end effector (16) also has a ledge (204) that is configured to cooperate with locking groove (202) when lockout mechanism (131) is engaged. In contrast, supporting structure (128) has a base surface (206) configured to cooperate with cam surface (200) when lockout lever (131) is not engaged.

C. Exemplary Actuation of Cartridge

In the present example, cartridge (28) is driven toward anvil (26) via closure member (54) until reaching the closed configuration with tissue positioned between cartridge (28) and anvil (26) as discussed above with respect to handle assembly (12). From the closed configuration, knife (32) and staple driver assembly (140) are further moved toward anvil (26) via firing bar (82) to form staples (not shown) in the tissue, fluidly seal the tissue, and sever the tissue for treating the patient. While actuation of cartridge (28) includes stapling and severing tissue in this example, it will be appreciated that one or more of these steps may be omitted from treatment as desired by the operator. Moreover, it will be appreciated that surgical stapling instrument (10) may be reconfigured to perform these steps simultaneously or sequentially as desired. For example, actuation of firing bar (82) causes driver assembly (140) and knife (32) to move distally toward anvil (26) in the present example. Alternatively, surgical stapling instrument (10) may be reconfigured to selectively fire one of staples (not shown) or knife (32), or selectively fire staples (not shown) and then knife (32), or vice versa. It should therefore be understood that the invention is not intended to be limited to the particular operation of surgical stapling instrument (10) or the associated treatment.

Figure 7B:
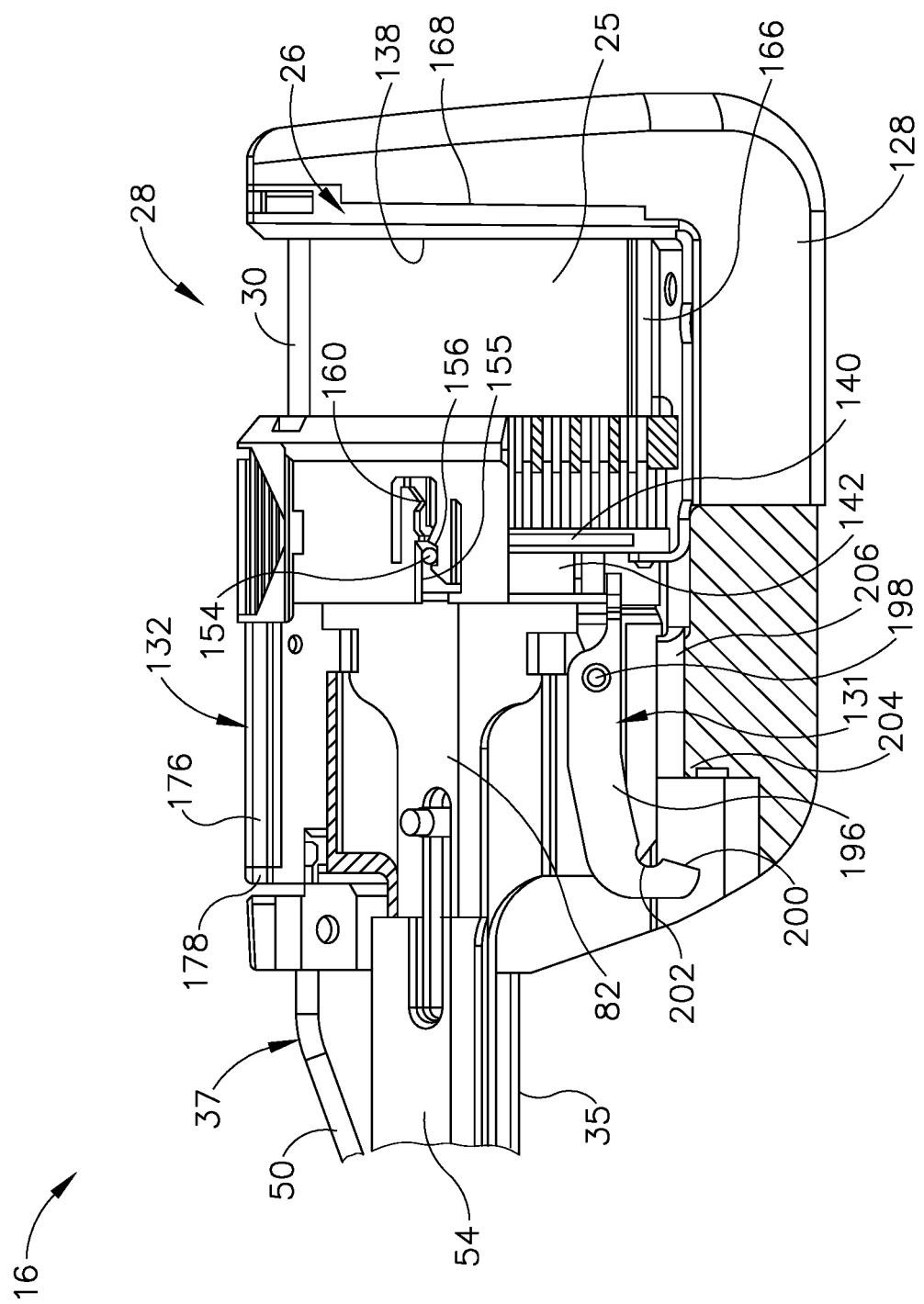
FIG. 7B depicts a left side view of the end effector of FIG. 1A with various components removed for clarity, and with the pin actuation mechanism in a closed position and the staple cartridge in the open position.

As shown in FIG. 7A, cartridge (28) is spaced proximally from anvil (26) to receive tissue within gap (25) in the open configuration. With tissue received between cartridge (28) and anvil (26), the operator manually directs push rod (50) distally via slide (18) as discussed above and shown in FIG. 7B. Push rod (50) is operatively connected to couplet (70) (see FIG. 6), which is connected to retaining pin (30). Thus, distally translating push rod (50) similarly translates retaining pin (30) to extend from cartridge (28) to anvil (26) and capture tissue between retaining pin (30) and guide pin (166).

Figure 7C:
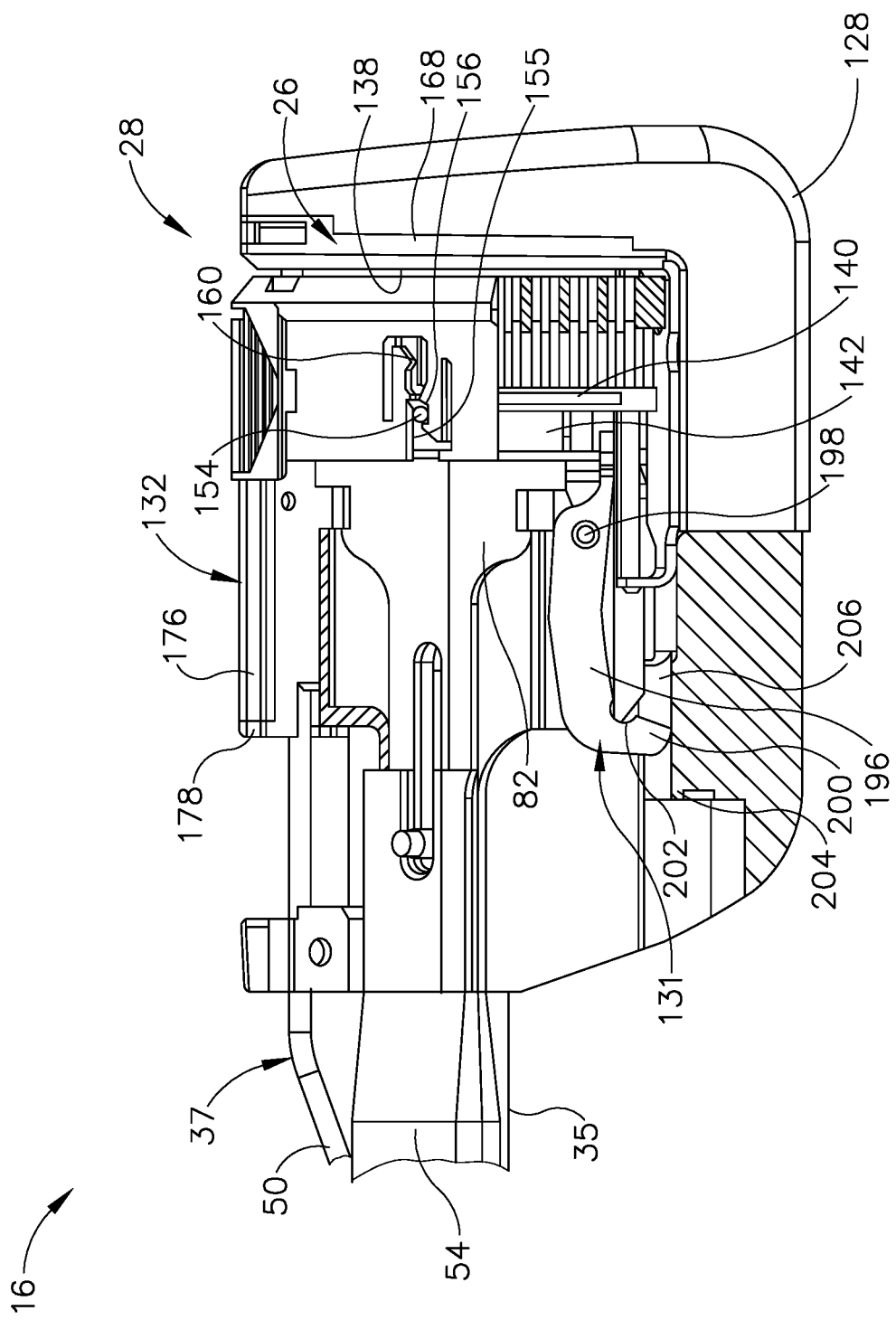
FIG. 7C depicts a left side view of the end effector of FIG. 1A with various components removed for clarity, and with the pin actuation mechanism in the closed position and the staple cartridge in the closed position via actuation of the closure mechanism.
Figure 7D:
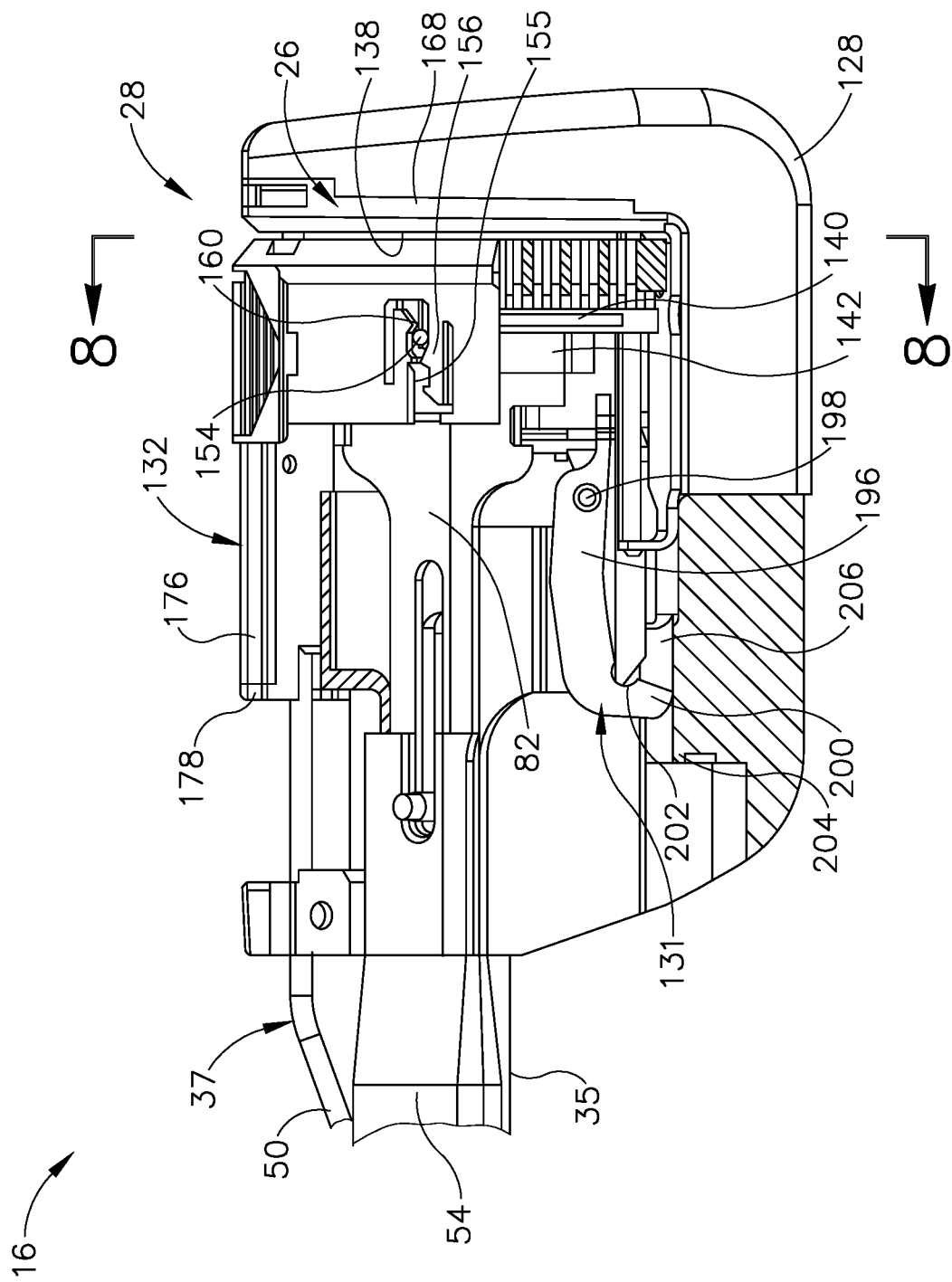
FIG. 7D depicts a left side view of the end effector of FIG. 1A with various components removed for clarity, and with the pin actuation mechanism and the staple cartridge in the closed positions and the firing trigger in the fired position for stapling and cutting tissue of a patient.
Figure 8:
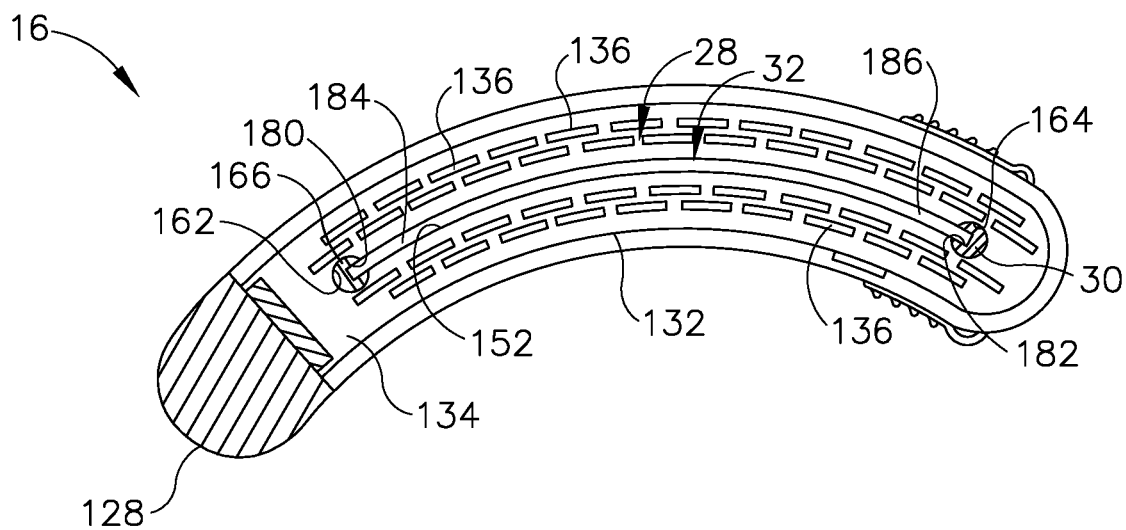
FIG. 8 depicts a cross-sectional view of the end effector of FIG. 7D, taken along section line 8-8 of FIG. 7D.
Figure 9:
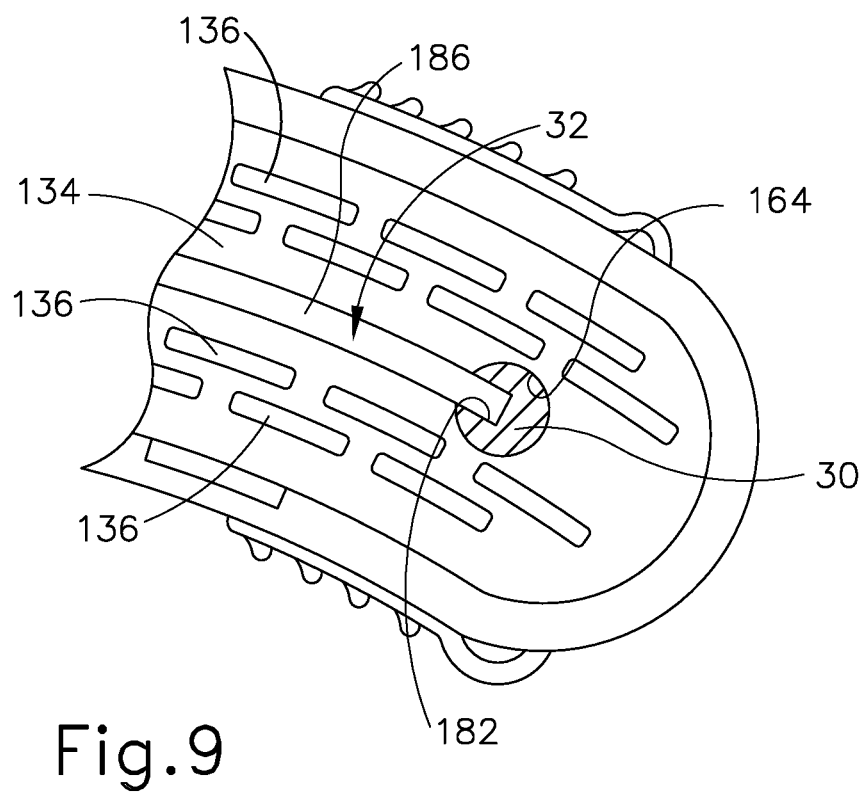
FIG. 9 depicts an enlarged cross-sectional view of a portion of the end effector of FIG. 8.

As shown in FIG. 7C, manipulation of closure trigger (20) (see FIG. 1C) forces closure member (54) to translate distally relative to supporting structure (128) of end effector (16). Closure member (54) supports cartridge (28) thereon such that distal translation of closure member (54) similarly moves firing bar (82) and cartridge (28) toward anvil (26). With cartridge (28) in the closed configuration and the tissue effectively captured in the end effector (16), the operator manipulates firing trigger (22) (see FIG. 1D) toward anvil (26) to the fired position. Distal translation of firing bar (82) causes firing bar (82) to engage knife holder (142), which supports both driver assembly (140) and knife (32) extending through driver assembly (140) as shown in FIG. 7D. In turn, driver assembly (140) directs staples (not shown) from staple slots (136) and against staple-forming surface (138) to form the staples (not shown) within the tissue for fluidly sealing the tissue. As the staples (not shown) are formed, knife (32) continues to translate distally through tissue and into anvil (26) to sever the fluidly sealed tissue. FIGS. 8-9 illustrate the fired cartridge (28) in greater detail, with knife (32) guided along cartridge housing slot (152), guide pin slot (180); and with retaining pin slot (182) between rows of staple slots (136) toward anvil (26).

Figure 10A:
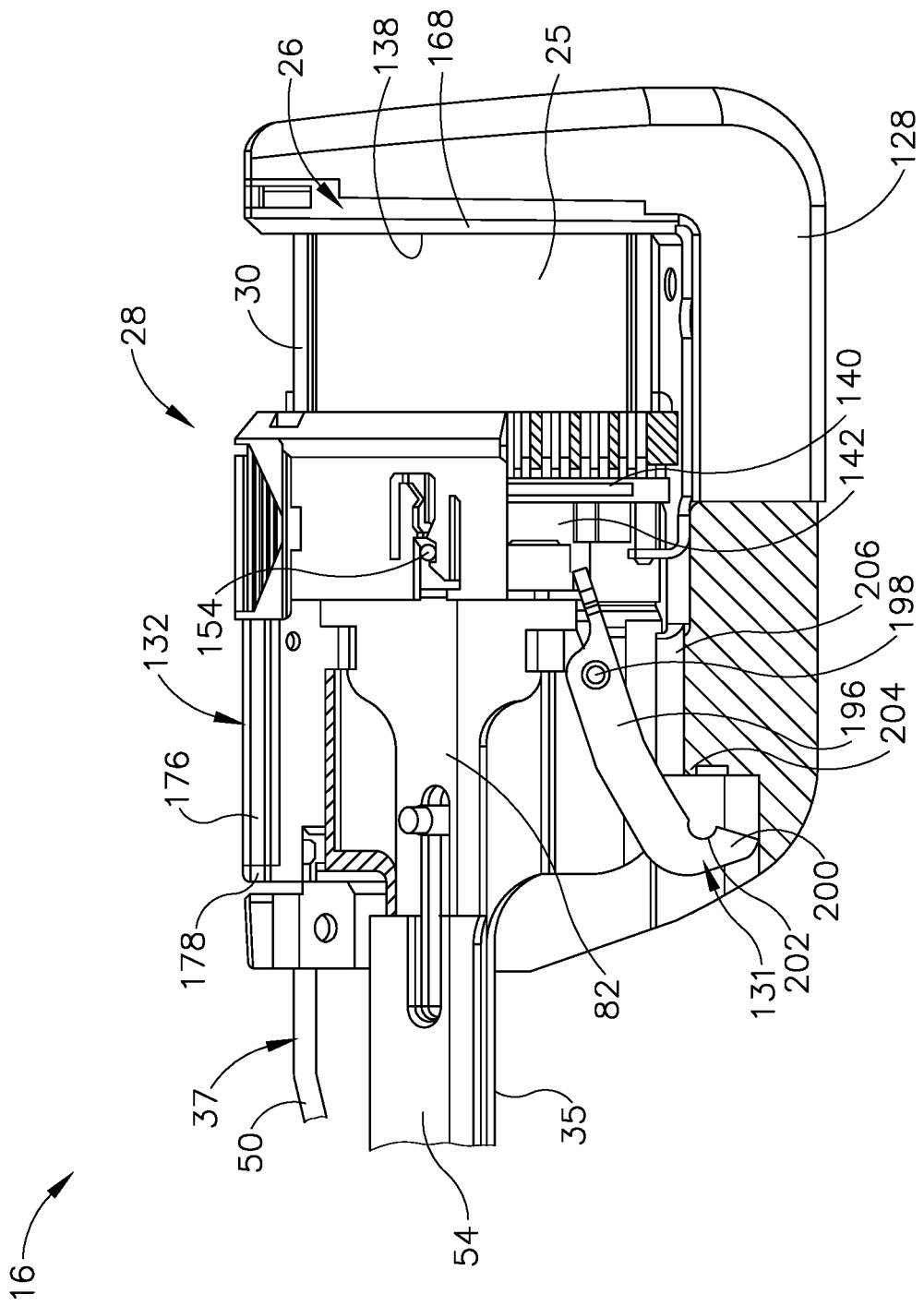
FIG. 10A depicts a left side view of the end effector of FIG. 1A, with various components removed for clarity, with the staple cartridge returned to the open position after actuating the firing trigger.
Figure 10B:
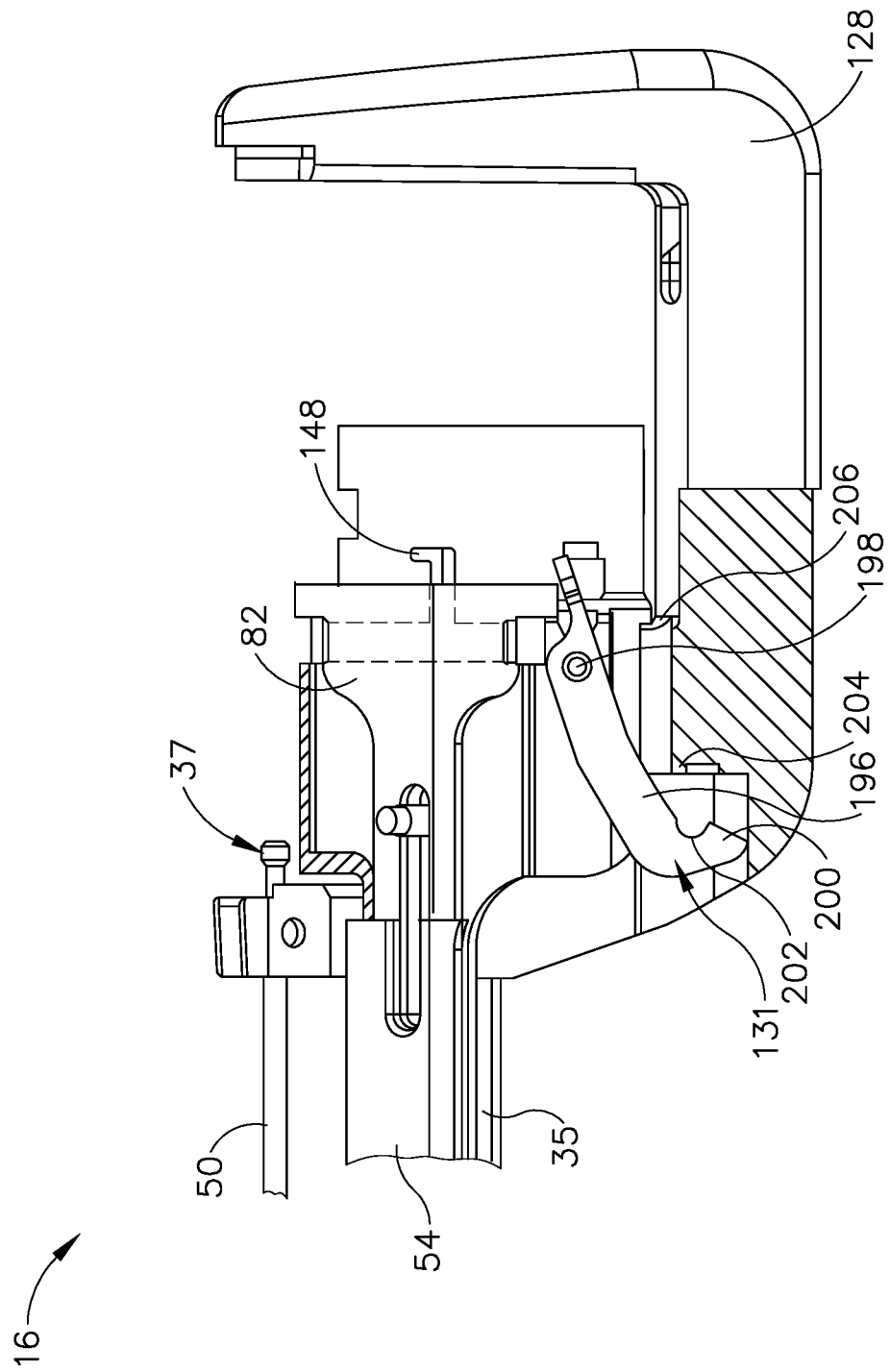
FIG. 10B depicts a left side view of the end effector of FIG. 1A, with various components removed for clarity, with the staple cartridge removed from the remainder of the end effector.
Figure 11:
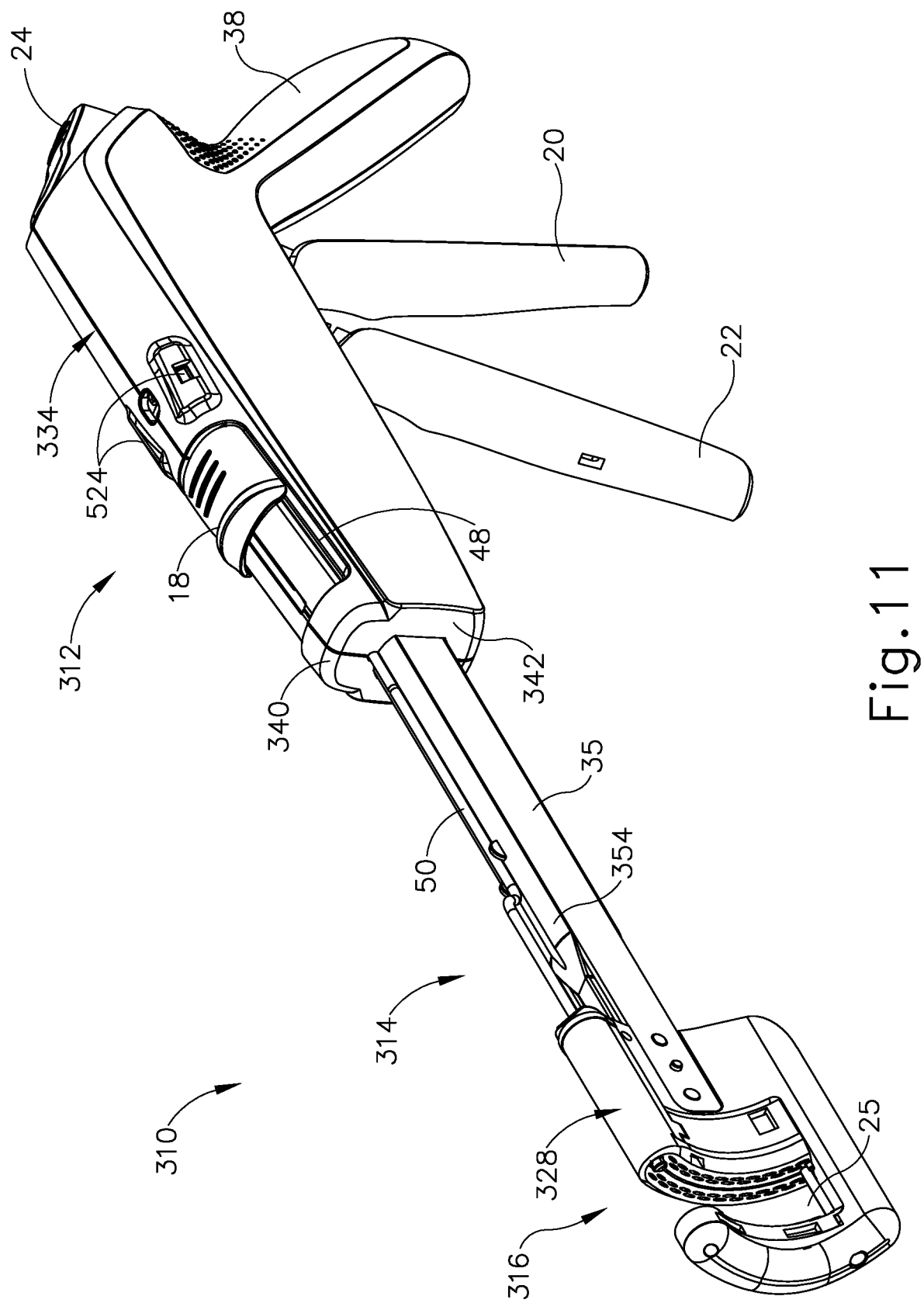
FIG. 11 depicts a right perspective view of another exemplary surgical stapling instrument.
Figure 12:
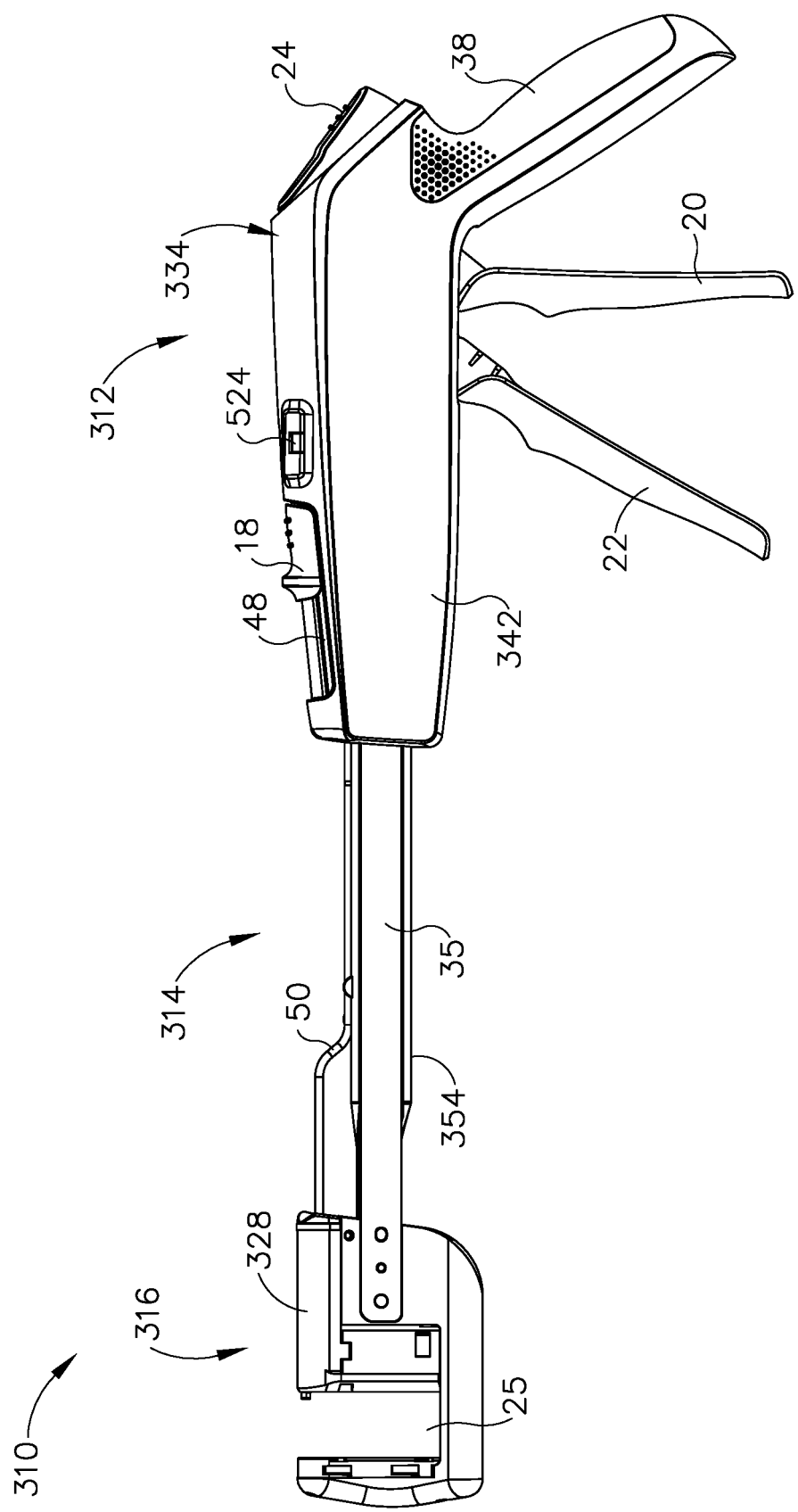
FIG. 12 depicts a right side view of the surgical stapling instrument of FIG. 11.

Once fired, the operator may depress release button (24) (see FIG. 2C) and withdraw closure member (54) and firing bar (82) proximally from the actuated, fired position to the unactuated position shown in FIGS. 10A-10B. More particularly, retractor hook (148) engages knife holder (142) to pull knife (32) proximally. At approximately the same time, as cartridge (28) translates proximally with closure member (54), lockout lever (196) of lockout mechanism (131) engages cartridge housing (132) to hold cartridge housing (132) in position. Thereby, the continued pull of knife (32) retracts knife (32) within cartridge housing (132) to inhibit unintended contact by operator with knife (32). Cartridge (28) may then be removed from supporting structure (128) of end effector (16), discarded, and replaced for further treatment if so desired. Of course, various suitable settings and procedures in which surgical stapling instrument (10) may be used will be apparent to those of ordinary skill in the art in view of the teachings herein.

It should also be understood that any other components or features of surgical stapling instrument (10) may be configured and operable in accordance with any of the various references cited herein. Additional exemplary modifications that may be provided for surgical stapling instrument (10) will be described in greater detail below. Various suitable ways in which the below teachings may be incorporated into surgical stapling instrument (10) will be apparent to those of ordinary skill in the art. Similarly, various suitable ways in which the below teachings may be combined with various teachings of the references cited herein will be apparent to those of ordinary skill in the art. It should also be understood that the below teachings are not limited to surgical stapling instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Surgical Stapling Instruments with Alternative End Effectors

While the above surgical stapling instrument (10) provides one example of end effector (16) projecting distally from handle assembly (12), it will be appreciated that the operator may desire an alternative end effector depending on one of a variety particular treatments. Various tissues may be more or less difficult to treat depending on size and/or density within the patient. Despite the operator properly positioning end effector (16) relative to tissue for accurately and precisely stapling and severing the tissue, thicker and/or denser tissues often require added force to be transmitted along surgical stapling instrument (10) and, in turn, may cause one or more components of instrument (10) to deform during use. For example, compressing a portion of the colon between anvil (26) and cartridge (28) in the closed configuration may deform supporting structure (128) of end effector (16), particularly as the tissue is stapled and severed. Thus, the particular location in which the staples form and the knife (32) cuts may vary or deviate a small, but relatively meaningful, amount that may negatively impact the effectiveness of the treatment.

While reducing deflection or deformation of end effector (16) by one or more structural modifications may increase accuracy and precision to improve treatment, it will be appreciated that some deflection or deformation may remain or even be desirable in some instances. In turn, rather than reduce deflection or deformation, end effector (16) may be augmented to accommodate such deflection or deformation. For example, staples may be driven to differing depths to correspondingly offset such deflection or deformation such that the staples are arranged more uniformly in the tissue of the patient. Alternatively, staples may be driven non-uniformly to differing depths to accommodate alternative staples of varying size or even to position the staples at varying depths within the patient as determined by the operator. It may therefore be desirable to provide surgical stapling instrument (310) with a staple driver assembly (440, 740, 1040) that is configured to offset deflection or deformation for uniformity; or provide varying desirable staple depths for one of any variety of patterns for non-uniformity, as discussed below.

End effector (316) is described below in the context of a proctocolectomy surgical procedure. While the following description of end effector (316) and methods of treatment is provided in the context of stapling and/or cutting colon tissue, it will be appreciated that surgical stapling instrument (310) and end effector (316) may be alternatively configured to treat any tissue in the human body with similar features. It should also be understood that the features discussed below may be readily incorporated into surgical stapling instrument (10) discussed above. To this end, like numbers indicate like features described above in greater detail.

A. Exemplary End Effector with Variable Height Driver Assembly

Figure 13:
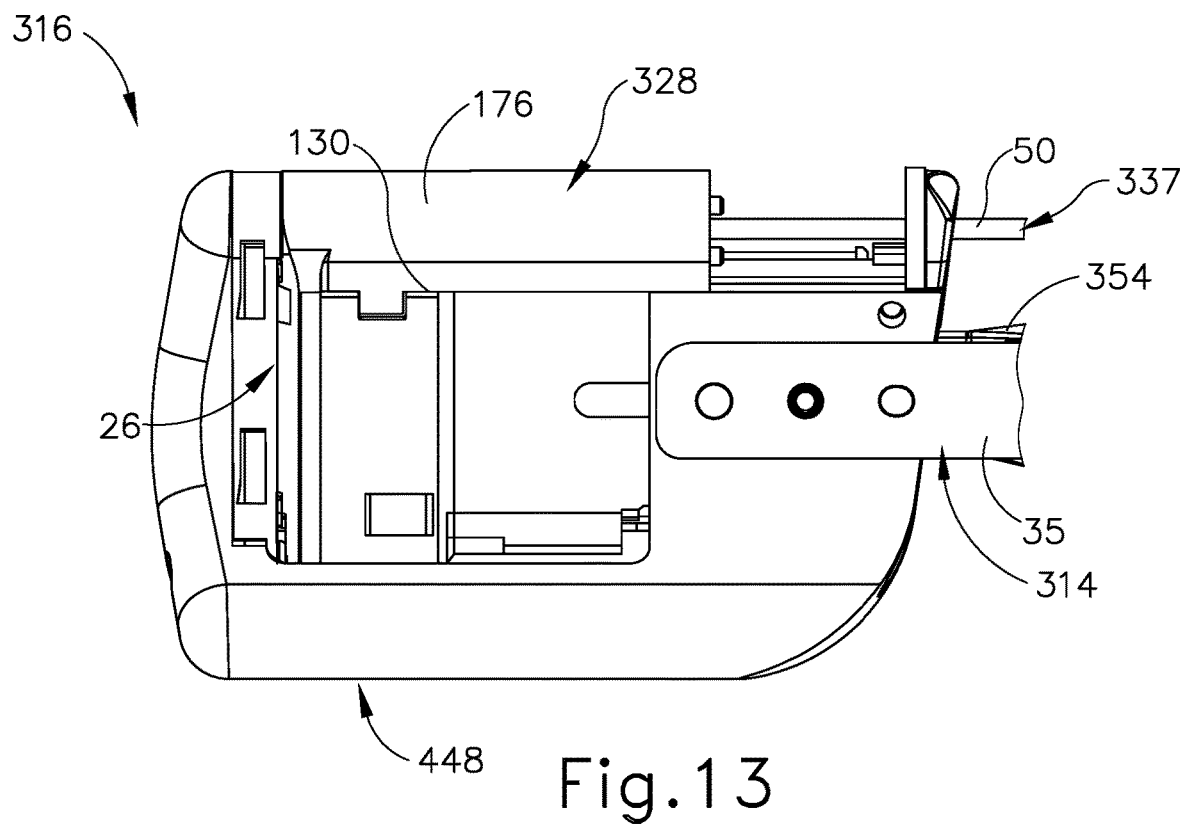
FIG. 13 depicts a right side view of an end effector of the surgical stapling instrument of FIG. 11 with a pin actuation mechanism in a closed position and a staple cartridge in a closed position.
Figure 14:
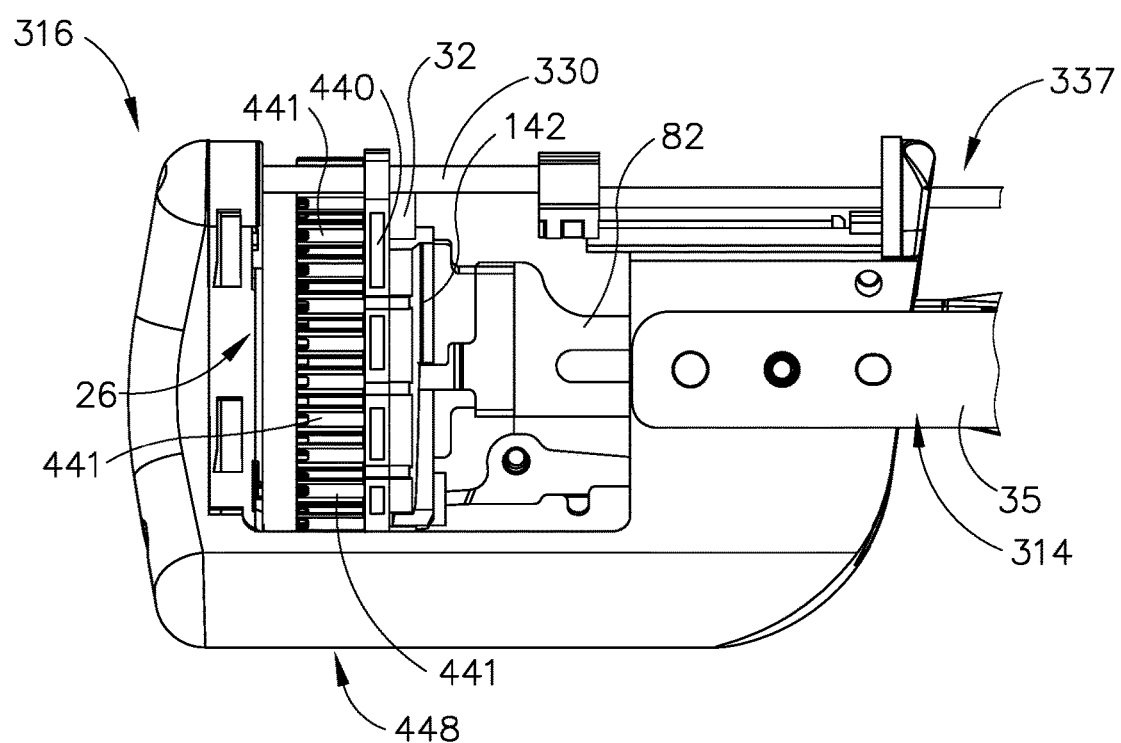
FIG. 14 depicts the end effector of FIG. 13 having a staple driver assembly with various components removed for clarity.

FIGS. 13 and 14 show end effector (316) extending distally from shaft assembly (314) as discussed above in greater detail. Cartridge (328) has been moved to the closed position for firing or actuating firing bar (82) distally to both form staples in the tissue with a driver assembly (440) and sever tissue with knife (32). With respect to staple formation, driver assembly (440) has a plurality of staple drivers (441) extending distally from a driver base (595) below corresponding staple containing slots (136) (see FIGS. 8-9). Each driver (441) has a groove (596) extending along a distal driver surface (597). Each groove (596) is configured to cradle a respective staple thereon for forcing the staple distally toward anvil (26) for formation. While driver assembly (440) has drivers (441) in a predetermined pattern with predetermined heights for various staple formations, it will be appreciated that alternative driver assemblies may be configured with other patterns or heights as contemplated herein to generate other desirable staple formations in tissue as determined to be desirable by the operator. Such predetermined patterns and heights of drivers (441) may also be referred to herein as a predetermined variable height pattern.

Driver assembly (440) of the present example has four offset rows of drivers (441), which will be referred to below as a "front outer row," a "front inner row," a "back outer row," and a "back inner row," that extend from a "left side" to a "right side." The terms "front outer row," "front inner row," "back outer row," "back inner row," are taken with respect to FIG. 13 with like terms being similarly used to describe alternative driver embodiments below. To this end, the terms "front row," "back row," "left side," and "right side" are for relative reference and not intended to unnecessarily limit the invention described herein.

The following examples include driver assemblies with drivers that have different heights (within the same driver assembly). Despite the fact that drivers within the same driver assembly have different heights in this example, these drivers assemblies are configured to ultimately provide formed staples in tissue having the same, uniform height. In other words, for any of the driver assemblies described below, the staples that are driven by the driver assembly will all have the same formed height, despite the fact that the drivers within the assembly have different heights. Drivers that are relatively short within a given driver assembly may have associated staples that are relatively tall. Conversely, drivers that are relatively tall within the same driver assembly may have associated staples that are relatively short. Thus, the unformed staple heights may vary based on variations in driver height, to ultimately yield formed staple heights that are all uniform. This may be desirable to account for uneven load distribution across the length and/or width of the staple driver, to account for variations in tissue thickness, etc. Alternatively, these drivers may be configured with like of varying heights to similarly provide formed staples in tissue having one or more varying, non-uniform height. Such variation may be desirable to accommodate deflection, produce varying forms of staples, or some combination thereof.

Figure 15:
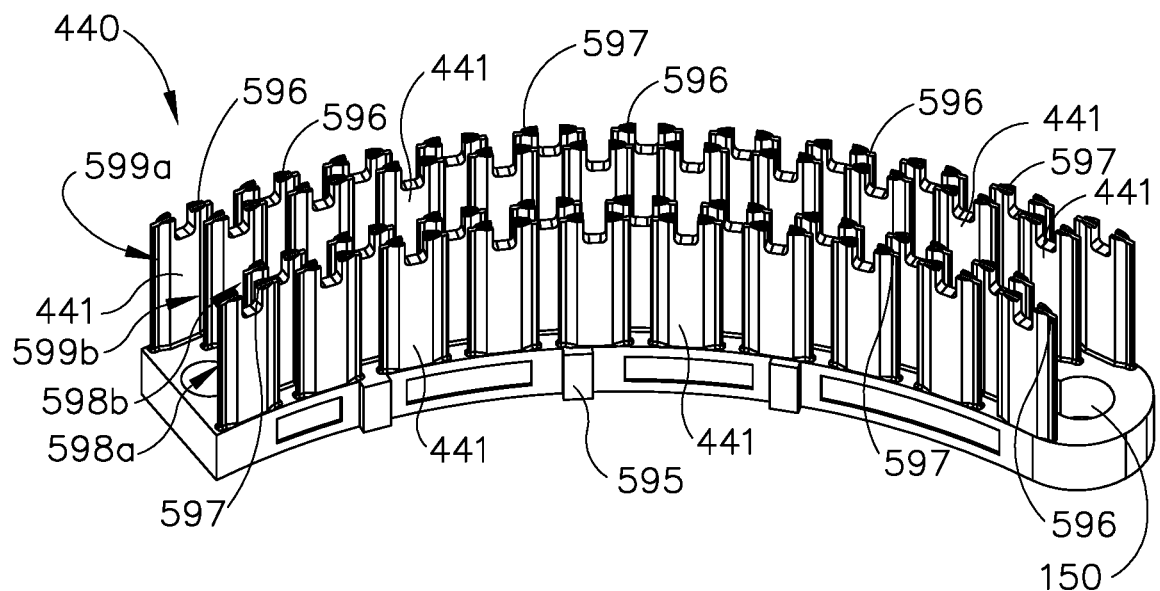
FIG. 15 depicts a right perspective view of the staple driver assembly of FIG. 14.

1. Exemplary Arcuate Driver Assembly with Variable Height Drivers in a First Predetermined Pattern Driver assembly (440) includes two pairs of offset rows of drivers (441) that are configured to direct two pairs of offset rows of staples in tissue for fluidly sealing tissue and inhibit fluid, such as blood, from leaking between the paired rows of staples. To this end, driver assembly (440) of FIG. 15 includes a front outer row (598a) of drivers positioned proximate to a front inner row (598b) on one side of slot (150) and a rear outer row (599a) positioned proximate to a rear inner row (599b) on an opposing side of slot (150). Thereby, drivers (441) are configured to form cooperating staple rows in tissue on each side of knife (32) (see FIG. 6) to fluidly seal the severed tissue on each severed end. In the present example, rows (598a, 598b, 599a, 598b) are arranged along a predetermined arcuate pattern having an inner radius of curvature of between approximately 1.0 inch and approximately 1.2 inches and an outer radius of curvature of between approximately 1.3 inches and approximately 1.5 inches. More particularly the inner radius of curvature is approximately 1.1 inches, and the outer radius of curvature is approximately 1.4 inches. However, it will be appreciated that drivers (441) may be alternatively arranged in other various predetermined patterns, such as other another arcuate pattern, a linear pattern, or some combination thereof.

Figure 16:
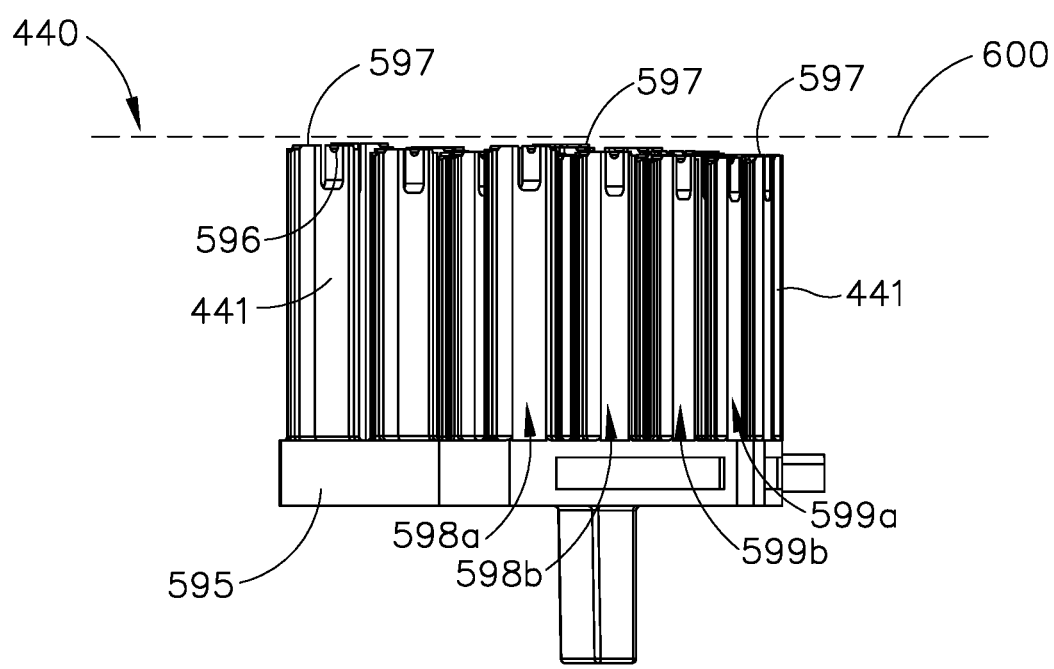
FIG. 16 depicts an upper side view of the staple driver assembly of FIG. 14.
Figure 17:
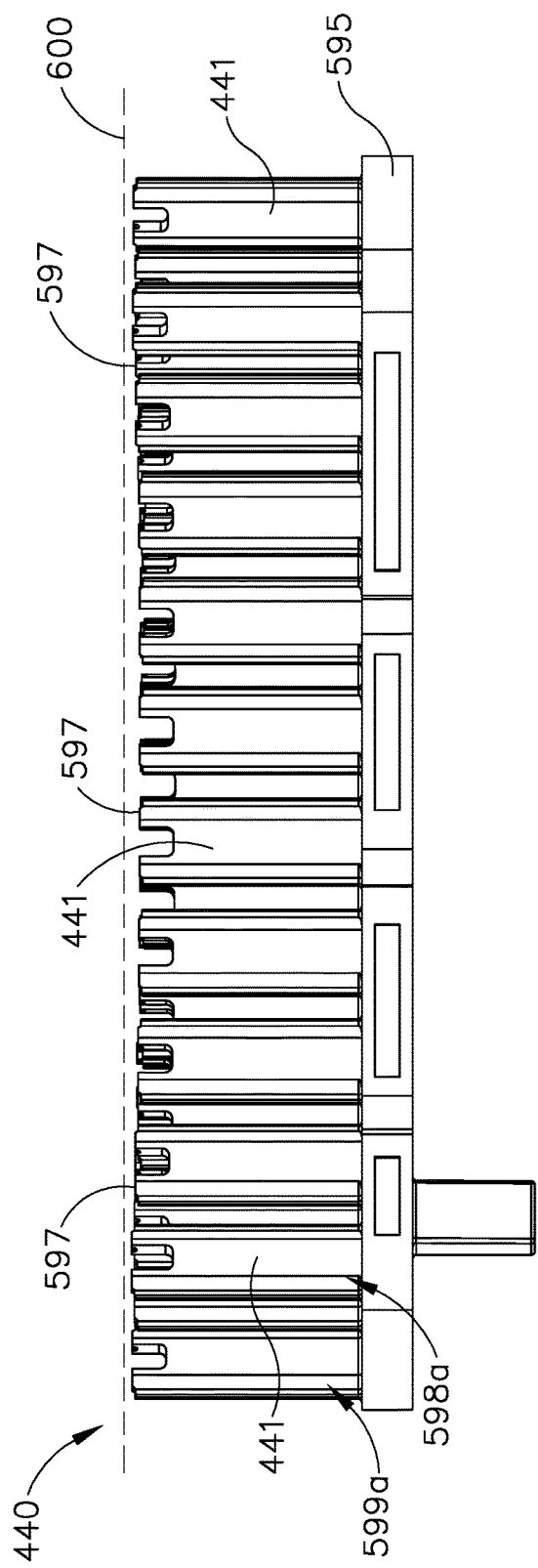
FIG. 17 depicts a right side view of the staple driver assembly of FIG. 14.
Figure 18:
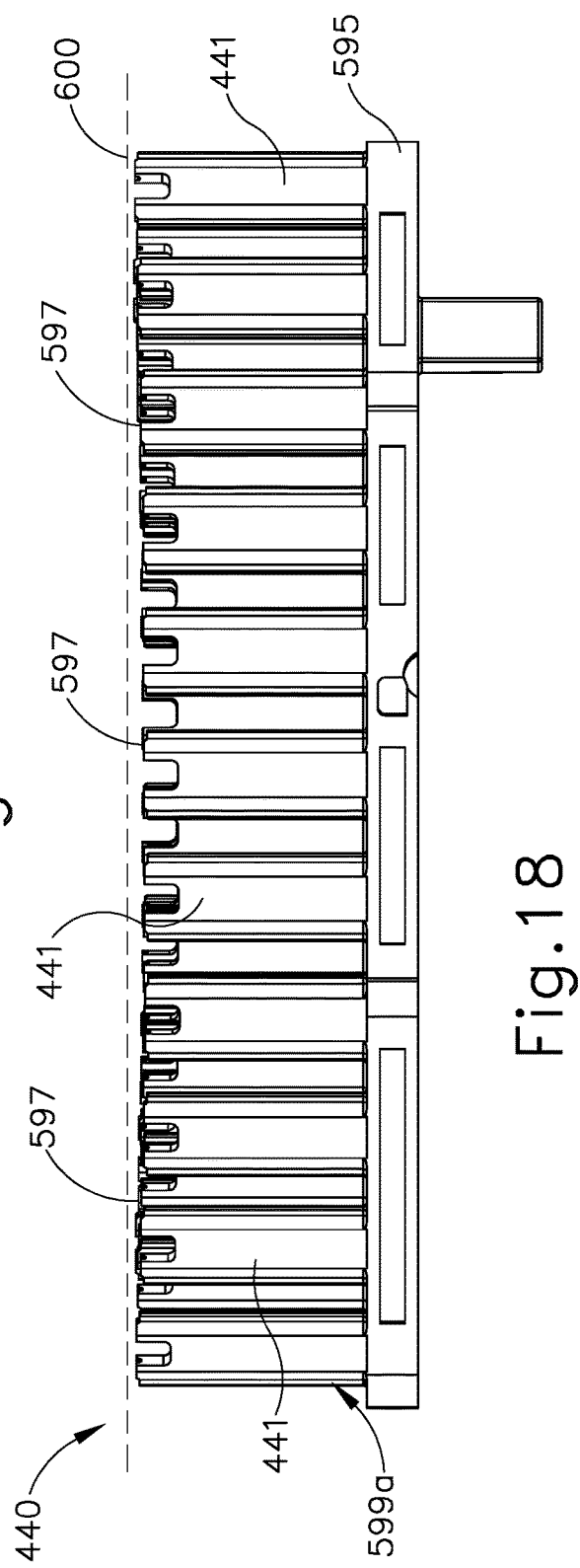
FIG. 18 depicts a left side view of the staple driver assembly of FIG. 14.

As shown in FIGS. 16-18, drivers (441) extend upwardly from driver base (595) with varying heights such that distal driver surfaces (597) collectively define a predetermined curvature that is configured to drive staples to various depths and/or offset a predetermined deflection relative to anvil (26) (see FIG. 14). Such predetermined curvature may extend in one dimension, two dimensions, or three dimensions along distal driver surfaces (597) of driver assembly (440). In other words, at least one driver (441) has a height larger or smaller than another driver (441).

For example, FIGS. 16-18 illustrate a reference plane (600) to more clearly show height differences among drivers (441). FIG. 16 shows a right side of driver assembly (440) having front outer and inner rows (598a, 598b) with a height that is greater than the heights of rear inner and outer rows (599b, 599a). More particularly, the varying height of drivers (441) tends to taper down from front outer row (598a) toward rear outer row (599a). As shown in FIGS. 17-18, each row (598a, 598b, 599a, 598b) of drivers (441) is configured with relatively larger drivers (441) to the left and right sides and relatively smaller drivers (441) in the middle between the left and right sides. Rows (598a, 598b, 599a, 598b) thus taper down from the left and right sides toward the middle.

Figure 19:
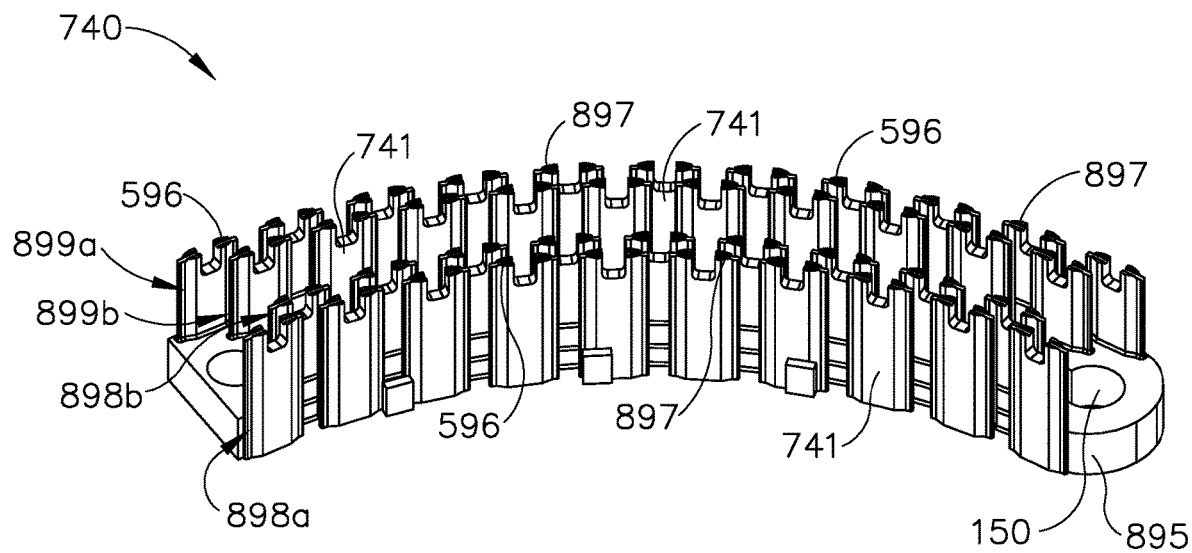
FIG. 19 depicts a right perspective view of another exemplary staple driver assembly.

2. Exemplary Arcuate Driver Assembly with Variable Height Drivers in a Second Predetermined Pattern Another exemplary driver assembly (740) shown in FIG. 19 includes two pairs of offset rows of drivers (741) that are configured to direct two pairs of offset rows of staples in tissue for fluidly sealing tissue and inhibit fluid, such as blood, from leaking between the paired rows of staples. To this end, driver assembly (740) of FIG. 19 includes a front outer row (898a) of drivers (741) that is positioned proximate to a front inner row (898b) on one side of slot (150); and a rear outer row (899a) that is positioned proximate to a rear inner row (899b) on an opposing side of slot (150). Drivers (741) are thereby configured to form cooperating staple rows in tissue on each side of knife (32) (see FIG. 6) to fluidly seal the severed tissue on each severed end. In the present example, rows (898a, 898b, 899a, 898b) are arranged along a predetermined arcuate pattern having an inner radius of curvature of between approximately 1.0 inch and approximately 1.2 inches and an outer radius of curvature of between approximately 1.3 inches and approximately 1.5 inches. More particularly the inner radius of curvature is approximately 1.1 inches, and the outer radius of curvature is approximately 1.4 inches. However, it will be appreciated that drivers (741) may be alternatively arranged in other various predetermined patterns, such as another arcuate pattern, a linear pattern, or some combination thereof.

Figure 20:
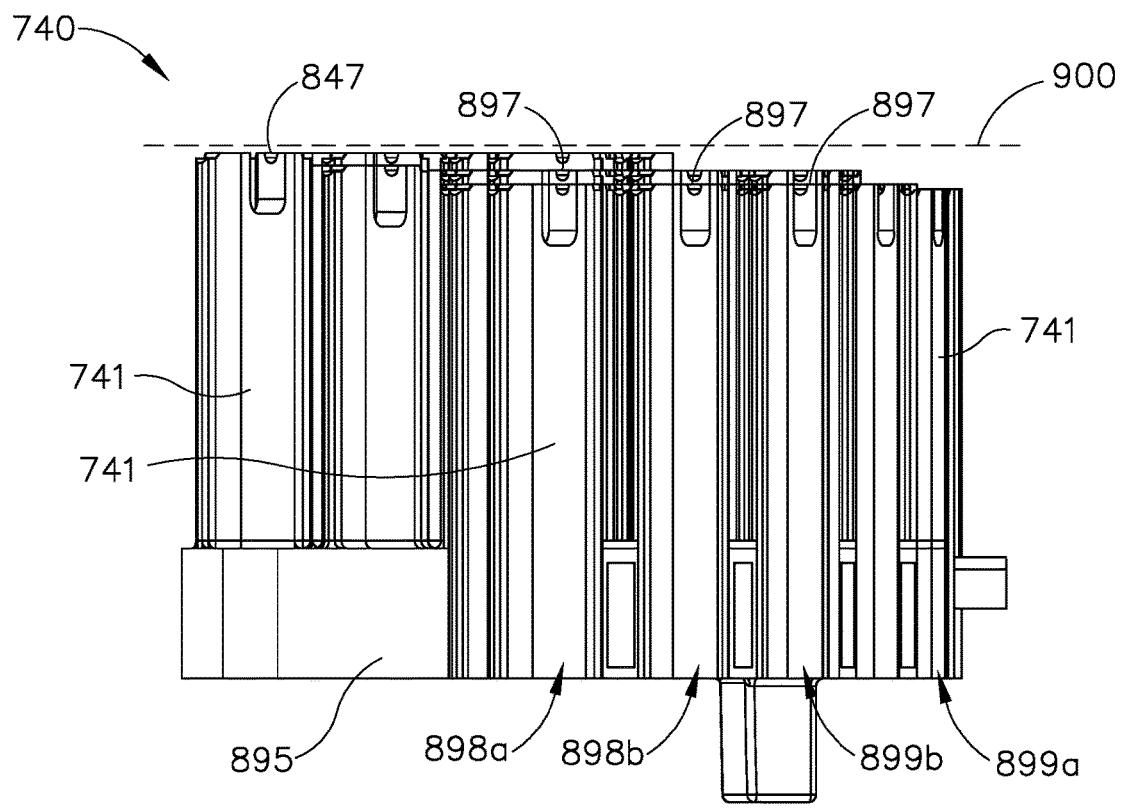
FIG. 20 depicts an upper side view of the staple driver assembly of FIG. 19.

As shown in FIGS. 20-22, drivers (741) extend upwardly from driver base (895) with varying heights such that distal driver surfaces (897) collectively define a predetermined curvature that is configured to drive staples to various depths and/or offset a predetermined deflection relative to anvil (26) (see FIG. 14). Such predetermined curvature may extend in one dimension, two dimensions, or three dimensions along distal driver surfaces (897) of driver assembly (740). In other words, at least one driver (741) has a height larger or smaller than another driver (741).

For example, FIGS. 20-22 illustrate a reference plane (900) to more clearly show height differences among drivers (741). FIG. 20 shows a right side of driver assembly (840) having front outer and inner rows (898*a*, 898*b*) with a height that is greater than the heights of rear inner and outer rows (899*b*, 899*a*). More particularly, the varying height of drivers (741) tends to taper down from front outer row (898*a*) toward rear outer row (899*a*). As shown in FIGS. 21-22, each row (898*a*, 898*b*, 899*a*, 898*b*) of drivers (741) has a generally uniform height from the left side to the right side despite having varying heights from front to rear.

Figure 23:
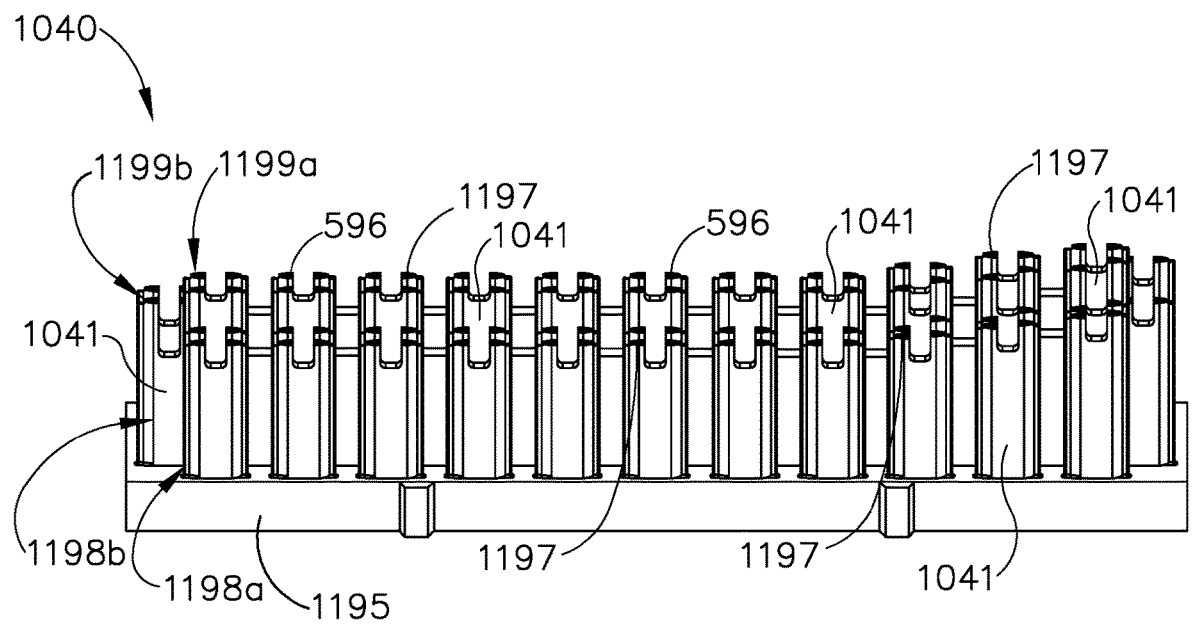
FIG. 23 depicts a right perspective view of another exemplary staple driver assembly.

3. Exemplary Linear Driver Assembly with Variable Height Drivers in a Third Predetermined Pattern Another exemplary driver assembly (1040) shown in FIG. 23 includes two pairs of offset rows of drivers (1041) that are configured to direct two pairs of offset rows of staples in tissue for fluidly sealing tissue and inhibit fluid, such as blood, from leaking between the paired rows of staples. To this end, driver assembly (1040) of FIG. 23 includes a front outer row (1198*a*) of drivers positioned proximate to a front inner row (1198*b*) on one side of slot (not shown) and a rear outer row (1199*a*) positioned proximate to a rear inner row (1199*b*) on an opposing side of slot (not shown). Drivers (1041) are thereby configured to form cooperating staple rows in tissue on each side of knife (32) (not shown) to fluidly seal the severed tissue on each severed end. In the present example, rows (1198*a*, 1198*b*, 1199*a*, 1198*b*) are arranged along a predetermined linear pattern. However, it will be appreciated that drivers (1041) may be alternatively arranged in other various predetermined patterns, such as another linear pattern, an arcuate pattern, or some combination thereof. It will be further appreciated that knife (not shown) and slot (not shown) may be configured to extend linearly but function similarly to slot (150) and knife (32) as shown in FIG. 6 and discussed above in greater detail.

Figure 24:
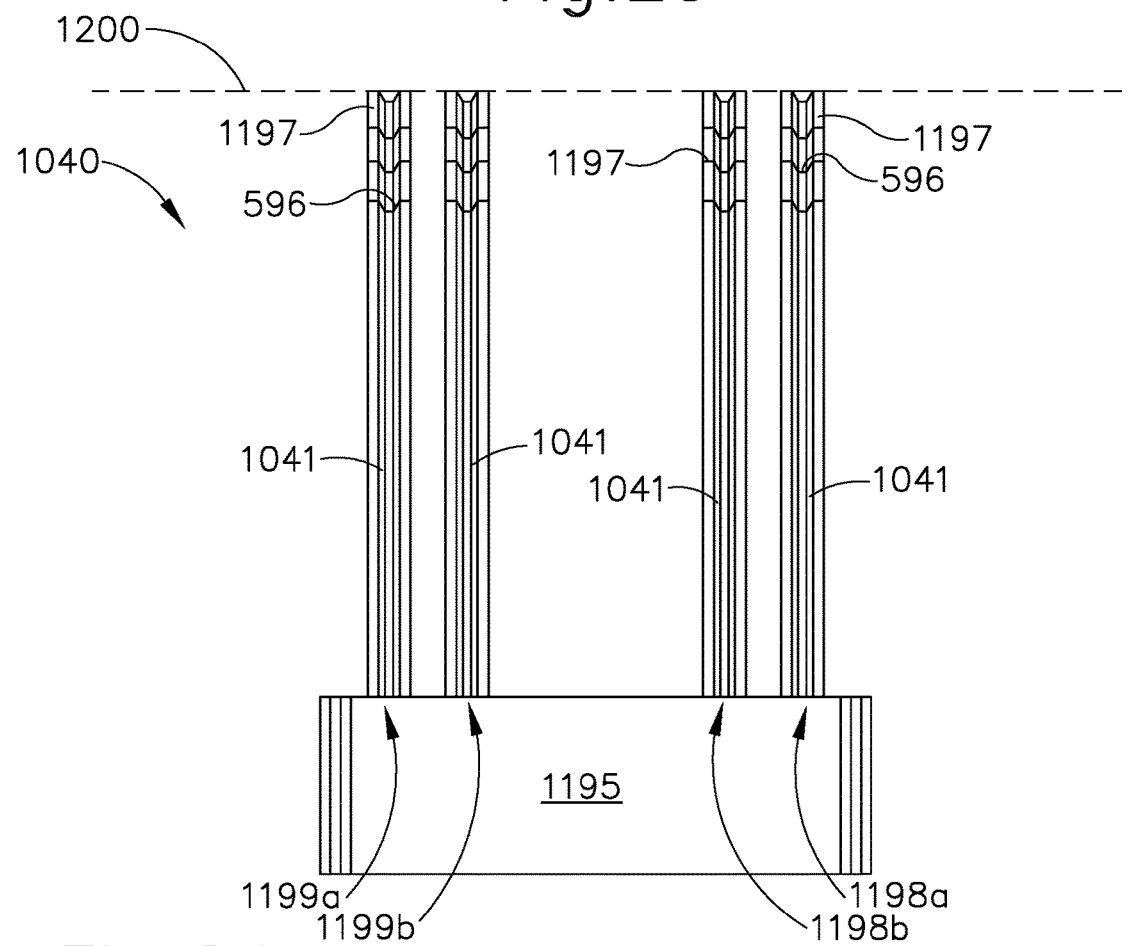
FIG. 24 depicts an upper side view of the staple driver assembly of FIG. 23.

As shown in FIGS. 24-26, drivers (1041) extend upwardly from driver base (1195) with varying heights such that distal driver surfaces (1197) collectively define a predetermined curvature that is configured to drive staples to various depths and/or offset a predetermined deflection relative to anvil (not shown). Such predetermined curvature may extend in one dimension, two dimensions, or three dimensions along distal driver surfaces (1197) of driver assembly (1040). In other words, at least one driver (1141) has a height larger or smaller than another driver (1141).

For example, FIGS. 24-26 illustrate a reference plane (1200) to more clearly show height differences among drivers (1141). FIG. 24 shows a side of driver assembly (1040) having front outer and inner rows (1198*a*, 1198*b*) and rear outer and inner rows (1199*a*, 1199*b*) with a generally uniform height, respectively, from the front side to the rear side despite having varying heights from left to right. As shown in FIGS. 25-26, each row (1198*a*, 1198*b*, 1199*a*, 1198*b*) of drivers (1041) is generally larger on the right side, tapers down toward the middle, and remains uniform from the middle to the right side.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a body having a firing mechanism configured to be selectively manipulated by an operator; (b) a shaft assembly extending distally from the body; (c) an end effector extending distally from the shaft assembly, the end effector including an anvil; and (d) a cartridge received within the end effector opposite the anvil and operatively connected to the firing mechanism, the cartridge including: (i) a cartridge housing having a plurality of staple slots, (ii) a plurality of staples respectively positioned within the plurality of staple slots, and (iii) a driver assembly having a plurality of drivers respectively supporting the plurality of staples thereon within the plurality of staple slots, wherein the firing mechanism is configured to selectively move the plurality of drivers distally toward the anvil for forming the plurality of staples therebetween, wherein at least one driver of the plurality of drivers has a variable distal height relative to at least another driver of the plurality of drivers in a predetermined variable height pattern.

Example 2

The surgical instrument of Example 1, wherein the predetermined variable height pattern of the plurality of drivers is configured to uniformly form the plurality of staples between the anvil and the driver assembly thereby accommodating deflection of the end effector.

Example 3

The surgical instrument of Example 1, wherein the predetermined variable height pattern of the plurality of drivers is configured to non-uniformly form the plurality of staples between the anvil and the driver assembly.

Example 4

The surgical instrument of any one or more of Examples 1 through 3, wherein the plurality of drivers includes a first row of drivers and a second row of drivers arranged in the predetermined variable height pattern, and wherein predetermined variable height pattern tapers down from the second row of drivers toward the first row of drivers.

Example 5

The surgical instrument of Example 4, wherein the first row of drivers has a first uniform distal height, wherein the second row of drivers has a second uniform distal height, and wherein the first uniform distal height is less than the second uniform distal height.

Example 6

The surgical instrument of Example 4, wherein the driver assembly has a knife slot configured to receive a knife therethrough, and the first and second rows of drivers are arranged on one side of the knife slot, wherein the plurality of drivers includes a third row of drivers and a fourth row of drivers arranged in the predetermined variable height pattern on another side of the knife slot, wherein the predetermined variable height pattern tapers down from the fourth row of drivers toward the third row of drivers.

Example 7

The surgical instrument of Example 6, wherein the first row of drivers has a first uniform distal height, wherein the second row of drivers has a second uniform distal height, wherein the first uniform distal height is less than the second uniform distal height, wherein the third row of drivers has a third uniform distal height, the fourth row of drivers has a fourth uniform distal height, and wherein the third uniform distal height is less than the fourth uniform distal height.

Example 8

The surgical instrument of Example 7, wherein the second uniform distal height is less than the third uniform distal height.

Example 9

The surgical instrument of any one or more of Examples 1 through 3, wherein the plurality of drivers includes a first row of drivers arranged in the predetermined variable height pattern from a first end to a second end and a middle therebetween, wherein the predetermined variable height pattern tapers down from the respective first and second ends toward the middle.

Example 10

The surgical instrument of Example 9, wherein the plurality of drivers includes a second row of drivers arranged in the predetermined variable height pattern from the first end to the second end and the middle therebetween, wherein the predetermined variable height pattern tapers down from the second row of drivers toward the first row of drivers.

Example 11

The surgical instrument of Example 10, wherein the driver assembly has a knife slot configured to receive a knife therethrough and the first and second rows of drivers are arranged on one side of the knife slot, wherein the plurality of drivers includes a third row of drivers and a fourth row of drivers arranged in the predetermined variable height pattern on another side of the knife slot from the first end to the second end and the middle therebetween, and wherein the predetermined variable height pattern tapers down from the fourth row of drivers toward the third row of drivers.

Example 12

The surgical instrument of any one or more of Examples 1 through 3, wherein the plurality of drivers includes a first row of drivers arranged in the predetermined variable height pattern from a first end to a second end and a middle therebetween, wherein the predetermined variable height pattern of the first row of drivers tapers down from the respective first end toward the middle and is generally uniform from the middle toward the second end.

Example 13

The surgical instrument of Example 12, wherein the plurality of drivers includes a second row of drivers arranged in the predetermined variable height pattern from the first end to the second end and a middle therebetween, and wherein the predetermined variable height pattern of the second row of drivers tapers down from the first end toward the middle and is generally uniform from the middle toward the second end.

Example 14

The surgical instrument of Example 13, wherein the first and second rows of drivers are identical.

Example 15

The surgical instrument of any one or more of Examples 13 through 14, wherein the driver assembly has a knife slot configured to receive a knife therethrough and the first and second rows of drivers are arranged on one side of the knife slot, wherein the plurality of drivers includes a third row of drivers and a fourth row of drivers arranged in the predetermined variable height pattern on another side of the knife slot from the first end to the second end and the middle therebetween, and wherein the predetermined variable height pattern of the third and fourth rows of drivers tapers down from the respective first end toward the middle and is generally uniform from the middle toward the second end.

Example 16

The surgical instrument of Example 15, wherein the first, second, third, and fourth rows of drivers are identical.

Example 17

A cartridge received in a surgical instrument, the cartridge comprising: (a) a cartridge housing having a plurality of staple slots; (b) a plurality of staples respectively positioned within the plurality of staple slots; and (c) a driver assembly having a plurality of drivers respectively supporting the plurality of staples thereon within the plurality of staple slots, wherein at least one driver of the plurality of drivers has a variable distal height relative to at least another driver of the plurality of drivers in a predetermined variable height pattern.

Example 18

A method of forming a plurality of staples in a tissue of a patient with a surgical instrument, the surgical instrument including a body have a firing mechanism configured to be selectively manipulated by an operator, a shaft assembly extending distally from the body, and a cartridge received within the end effector opposite the anvil and operatively connected to the firing mechanism, the cartridge having a cartridge housing with a plurality of staple slots, a plurality of staples respectively position within the plurality of staple slots, and a driver assembly with a plurality of drivers respectively supporting the plurality of staples thereon within the plurality of staple slots, wherein the firing mechanism is configured to selectively move the plurality of drivers distally toward the anvil for forming the staples therebetween, wherein at least one driver of the plurality of drivers has a variable distal height relative to at least another driver of the plurality of drivers in a predetermined variable height pattern, the method comprising: (a) selectively manipulating the firing mechanism and directing the plurality of drivers with the respective plurality of staples toward the anvil in the predetermined variable height pattern; (b) pressing the plurality of staples between the driver assembly and anvil; and (c) forming the plurality of staples within the tissue of the patient and thereby fluidly sealing the tissue along the formed plurality of staples therewith.

Example 19

The method of Example 18, further comprising deflecting a portion of the end effector with the anvil relative to the plurality of drivers a predetermined deflection such that the predetermined variable height pattern accommodates the predetermined deflection, and wherein forming the plurality of staples further includes uniformly forming the plurality of staples within the tissue.

Example 20

The method of Example 18, wherein forming the plurality of staples further includes non-uniformly forming the plurality of staples within the tissue.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

The entire disclosures of: U.S. Pat. No. 5,403,312, entitled "Electrosurgical Hemostatic Device," which issued on Apr. 4, 1995; U.S. Pat. No. 7,000,818, entitled "Surgical Stapling Instrument having Separate Distinct Closing and Firing Systems," which issued on Feb. 21, 2006; U.S. Pat. No. 7,422,139, entitled "Motor-Driven Surgical Cutting and Fastening Instrument with Tactile Position Feedback," which issued on Sep. 9, 2008; U.S. Pat. No. 7,464,849, entitled "Electro-Mechanical Surgical Instrument with Closure System and Anvil Alignment Components," which issued on Dec. 16, 2008; U.S. Pat. No. 7,670,334, entitled "Surgical Instrument Having An Articulating End Effector," which issued on Mar. 2, 2010; U.S. Pat. No. 7,753,245, entitled "Surgical Stapling Instruments," which issued on Jul. 13, 2010 U.S. Pat. No. 8,393,514, entitled "Selectively Orientable Implantable Fastener Cartridge," which issued on Mar. 12, 2013 U.S. patent application Ser. No. 11/343,803, entitled "Surgical Instrument Having Recording Capabilities;" now U.S. Pat. No. 7,845,537; U.S. patent application Ser. No. 12/031,573, entitled "Surgical Cutting And Fastening Instrument Having RF Electrodes," filed Feb. 14, 2008, now abandoned; U.S. patent application Ser. No. 12/031,873, entitled "End Effectors For A Surgical Cutting And Stapling Instrument," filed Feb. 15, 2008, now U.S. Pat. No. 7,980,443; U.S. patent application Ser. No. 12/235,782, entitled "Motor-Driven Surgical Cutting Instrument," now U.S. Pat. No. 8,210,411; U.S. patent application Ser. No. 12/249,117, entitled "Powered Surgical Cutting And Stapling Apparatus With Manually Retractable Firing System," now U.S. Pat. No. 8,608,045; U.S. patent application Ser. No. 12/647,100, entitled "Motor-Driven Surgical Cutting Instrument with Electric Actuator Directional Control Assembly," filed Dec. 24, 2009; now U.S. Pat. No. 8,220,688; U.S. patent application Ser. No. 12/893,461, entitled "Staple Cartridge," filed Sep. 29, 2012, now U.S. Pat. No. 8,733,613; U.S. patent application Ser. No. 13/036,647, entitled "Surgical Stapling Instrument," filed Feb. 28, 2011, now U.S. Pat. No. 8,561,870; U.S. patent application Ser. No. 13/118,241, entitled "Surgical Stapling Instruments With Rotatable Staple Deployment Arrangements," now U.S. Patent Application Publication No. 2012/0298719, issued as U.S. Pat. No. 9,072,535 on Jul. 7, 2015; U.S. patent application Ser. No. 13/524,049, entitled "Articulatable Surgical Instrument Comprising A Firing Drive," filed on Jun. 15, 2012; now U.S. Patent Application Publication No. 2013/0334278, issued as U.S. Pat. No. 9,101,358 on Aug. 11, 2015; U.S. patent application Ser. No. 13/800,025, entitled "Staple Cartridge Tissue Thickness Sensor System," filed on Mar. 13, 2013, now U.S. Patent Application Publication No. 2014/0263551, issued as U.S. Pat. No. 9,345,481 on May 24, 2016; U.S. patent application Ser. No. 13/800,067, entitled "Staple Cartridge Tissue Thickness Sensor System," filed on Mar. 13, 2013, now U.S. Patent Application Publication No. 2014/0263552, now abandoned; U.S. Patent Application Publication No. 2007/0175955, entitled "Surgical Cutting And Fastening Instrument With Closure Trigger Locking Mechanism," filed Jan. 31, 2006, now abandoned; and U.S. Patent Application Publication No. 2010/0264194, entitled "Surgical Stapling Instrument With An Articulatable End Effector," filed Apr. 22, 2010, now U.S. Pat. No. 8,308,040, are hereby incorporated by reference herein.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a body having a firing mechanism configured to be selectively manipulated by an operator;
   (b) a shaft assembly extending distally from the body;
   (c) an end effector extending distally from the shaft assembly, the end effector including an anvil configured to deflect a predetermined deflection against a tissue compressed thereagainst; and
   (d) a cartridge received within the end effector opposite the anvil and operatively connected to the firing mechanism, the cartridge including:
      (i) a cartridge housing having a plurality of staple slots,
      (ii) a plurality of staples respectively positioned within the plurality of staple slots, and
      (iii) a driver assembly having a driver base and a plurality of drivers extending in a distal direction therefrom, wherein the plurality of the drivers respectively support the plurality of staples thereon within the plurality of staple slots, wherein the firing mechanism is configured to selectively move the plurality of drivers distally toward the anvil for forming the plurality of staples therebetween, wherein at least one driver of the plurality of drivers has a first distal height that is different relative to a second distal height of at least another driver of the plurality of drivers in a predetermined varied height pattern,
   wherein the plurality of drivers includes a first row of drivers and a second row of drivers arranged on the driver base in the predetermined varied height pattern, and wherein predetermined varied height pattern tapers down from the second row of drivers toward the first row of drivers.

2. The surgical instrument of claim 1, wherein the predetermined varied height pattern of the plurality of drivers is configured to uniformly form the plurality of staples between the anvil and the driver assembly thereby accommodating deflection of the end effector.

3. The surgical instrument of claim 1, wherein the predetermined varied height pattern of the plurality of drivers is configured to non-uniformly form the plurality of staples between the anvil and the driver assembly.

4. The surgical instrument of claim 1, wherein the first row of drivers has a first uniform distal height, wherein the second row of drivers has a second uniform distal height, and wherein the first uniform distal height is less than the second uniform distal height.

5. The surgical instrument of claim 1, wherein the driver base has a knife slot configured to receive a knife therethrough, and the first and second rows of drivers are arranged on one side of the knife slot, wherein the plurality of drivers includes a third row of drivers and a fourth row of drivers arranged on the driver base in the predetermined varied height pattern on another side of the knife slot, wherein the predetermined varied height pattern tapers down from the fourth row of drivers toward the third row of drivers.

6. The surgical instrument of claim 5, wherein the first row of drivers has a first uniform distal height, wherein the second row of drivers has a second uniform distal height, wherein the first uniform distal height is less than the second uniform distal height, wherein the third row of drivers has a third uniform distal height, the fourth row of drivers has a fourth uniform distal height, and wherein the third uniform distal height is less than the fourth uniform distal height.

7. The surgical instrument of claim 6, wherein the second uniform distal height is less than the third uniform distal height.

8. The surgical instrument of claim 6, wherein the first row of drivers extends parallel to the second row of drivers.

9. The surgical instrument of claim 5, wherein the first, second, third, and fourth rows are arranged along a predetermined arcuate pattern having an inner radius of curvature of between approximately 1.0 inch and approximately 1.2 inches and an outer radius of curvature of between approximately 1.3 inches and approximately 1.5 inches.

10. The surgical instrument of claim 9, wherein the inner radius of curvature is approximately 1.1 inches and the outer radius of curvature is approximately 1.4 inches.

11. The surgical instrument of claim 1, wherein the driver base defines a knife slot configured to movably receive a knife therethrough, wherein the plurality of drivers includes a first row of drivers and a second row of drivers arranged on the driver base in the predetermined varied height pattern from a first end to a second end and a middle therebetween, and wherein the first row of drivers is arranged on one side of the knife slot and the second row of drivers is arranged on another side of the knife slot.

12. The surgical instrument of claim 11, wherein the knife slot is configured to movably receive a retaining pin therethrough.

13. A surgical instrument comprising:
(a) a body having a firing mechanism configured to be selectively manipulated by an operator;
(b) a shaft assembly extending distally from the body;
(c) an end effector extending distally from the shaft assembly, the end effector including an anvil configured to deflect a predetermined deflection against a tissue compressed thereagainst; and
(d) a cartridge received within the end effector opposite the anvil and operatively connected to the firing mechanism, the cartridge including:
  (i) a cartridge housing having a plurality of staple slots,
  (ii) a plurality of staples respectively positioned within the plurality of staple slots, and
  (iii) a driver assembly having a driver base and a plurality of drivers extending in a distal direction therefrom, wherein the plurality of the drivers respectively support the plurality of staples thereon within the plurality of staple slots, wherein the firing mechanism is configured to selectively move the plurality of drivers distally toward the anvil for forming the plurality of staples therebetween, wherein at least one driver of the plurality of drivers has a first distal height that is different relative to a second distal height of at least another driver of the plurality of drivers in a predetermined varied height pattern,
wherein the plurality of drivers includes a first row of drivers arranged on the driver base in the predetermined varied height pattern from a first end to a second end and a middle therebetween, wherein the predetermined varied height pattern of the first row of drivers tapers down from the respective first end toward the middle and is generally uniform from the middle toward the second end.

14. The surgical instrument of claim 13, wherein the predetermined varied height pattern of the plurality of drivers is configured to uniformly form the plurality of staples between the anvil and the driver assembly thereby accommodating deflection of the end effector.

15. The surgical instrument of claim 13, wherein the predetermined varied height pattern of the plurality of drivers is configured to non-uniformly form the plurality of staples between the anvil and the driver assembly.

16. The surgical instrument of claim 13, wherein the plurality of drivers includes a second row of drivers arranged on the driver base in the predetermined varied height pattern from the first end to the second end and a middle therebetween, and wherein the predetermined varied height pattern of the second row of drivers tapers down from the first end toward the middle and is generally uniform from the middle toward the second end.

17. The surgical instrument of claim 16, wherein the driver base has a knife slot configured to receive a knife therethrough and the first and second rows of drivers are arranged on one side of the knife slot, wherein the plurality of drivers includes a third row of drivers and a fourth row of drivers arranged on the driver base in the predetermined varied height pattern on another side of the knife slot from the first end to the second end and the middle therebetween, and wherein the predetermined varied height pattern of the third and fourth rows of drivers tapers down from the respective first end toward the middle and is generally uniform from the middle toward the second end.

18. The surgical instrument of claim 17, wherein the first, second, third, and fourth rows are arranged along a predetermined arcuate pattern having an inner radius of curvature of between approximately 1.0 inch and approximately 1.2 inches and an outer radius of curvature of between approximately 1.3 inches and approximately 1.5 inches.

19. The surgical instrument of claim 18, wherein the inner radius of curvature is approximately 1.1 inches and the outer radius of curvature is approximately 1.4 inches.

20. A cartridge configured to be received in a surgical instrument, the cartridge comprising:
(a) a cartridge housing having a plurality of staple slots;
(b) a plurality of staples respectively positioned within the plurality of staple slots; and
(c) a driver assembly having a driver base defining a knife slot configured to receive a knife therethrough and a plurality of drivers extending from the driver base, wherein the plurality of drivers respectively support the plurality of staples thereon within the plurality of staple slots, wherein at least one driver of the plurality of drivers has a first distal height that is different relative to a second distal height of at least another driver of the plurality of drivers in a predetermined varied height pattern,
wherein the plurality of drivers includes at least first, second, third, and fourth row of drivers arranged on the driver base in the predetermined varied height pattern, and wherein the first and second rows of drivers are arranged on one side of the knife slot, wherein the third and fourth rows of drivers are arranged on another side of the knife slot, wherein predetermined varied height pattern tapers down from the second row of drivers toward the first row of drivers, wherein the predetermined varied height pattern tapers down from the fourth row of drivers toward the third row of drivers.

* * * * *